US010980568B1

(12) United States Patent
Murphy

(10) Patent No.: US 10,980,568 B1
(45) Date of Patent: Apr. 20, 2021

(54) HALF HANDLE BONE ACCESS NEEDLE

(71) Applicant: IZI MEDICAL PRODUCTS, LLC, Owings Mills, MD (US)

(72) Inventor: Kieran Murphy, Towson, MD (US)

(73) Assignee: IZI Medical Products, LLC, Owings Mills, MD (US)

( * ) Notice: Subject to any disclaimer, the term of this patent is extended or adjusted under 35 U.S.C. 154(b) by 0 days.

(21) Appl. No.: 16/694,003

(22) Filed: Nov. 25, 2019

(51) Int. Cl.
*A61B 17/34* (2006.01)
*A61B 10/02* (2006.01)
*A61B 17/88* (2006.01)
*A61B 17/00* (2006.01)

(52) U.S. Cl.
CPC ........ *A61B 17/3417* (2013.01); *A61B 10/025* (2013.01); *A61B 17/3472* (2013.01); *A61B 17/3496* (2013.01); *A61B 17/8811* (2013.01); *A61B 17/8819* (2013.01); *A61B 2010/0258* (2013.01); *A61B 2017/00424* (2013.01); *A61B 2017/00477* (2013.01); *A61B 2017/346* (2013.01); *A61B 2017/347* (2013.01)

(58) Field of Classification Search
CPC ............ A61B 17/3417; A61B 17/3472; A61B 17/3496; A61B 17/8811; A61B 17/8819; A61B 2017/00424; A61B 2017/00477; A61B 2017/346; A61B 2017/347; A61B 10/025; A61B 2010/0258
See application file for complete search history.

(56) References Cited

U.S. PATENT DOCUMENTS

| 6,312,394 | B1 | 11/2001 | Fleming, III |
| 6,752,791 | B2 | 6/2004 | Murphy |
| 8,834,481 | B2 | 9/2014 | Murphy |
| 9,289,235 | B2 | 3/2016 | Murphy |
| 9,375,203 | B2 | 6/2016 | Murphy |
| 9,427,254 | B2 | 8/2016 | Murphy |
| 2004/0153138 | A1 | 8/2004 | Murphy |
| 2008/0200916 | A1 | 8/2008 | Murphy |
| 2012/0059380 | A1 | 3/2012 | Deangelo et al. |
| 2018/0146982 | A1 | 5/2018 | Brockman et al. |
| 2018/0206967 | A1 | 7/2018 | Duc et al. |

FOREIGN PATENT DOCUMENTS

| WO | 9918865 A1 | 4/1999 |
| WO | 9918866 A1 | 4/1999 |

OTHER PUBLICATIONS

International Search Report and Written Opinion issued in corresponding PCT/IB2019/060183 dated Aug. 24, 2020.

*Primary Examiner* — Devin B Henson
(74) *Attorney, Agent, or Firm* — Miles & Stockbridge P.C.; Ajay A. Jagtiani

(57) ABSTRACT

A handle device is provided comprising a first wing and a second wing. The first wing and the second wing are configured to pivot about a common axis to one another. The first wing has one or more first ridge, and a first one or more clearance spaces. The second wing has one or more second ridges and a second one or more clearance spaces. The one or more first ridges is configured to be received within the second one or more clearance spaces and the one or more second ridges is configured to be received within the first one or more clearance spaces when the first wing is pivoted about the common axis to the second wing in a folded configuration.

20 Claims, 19 Drawing Sheets

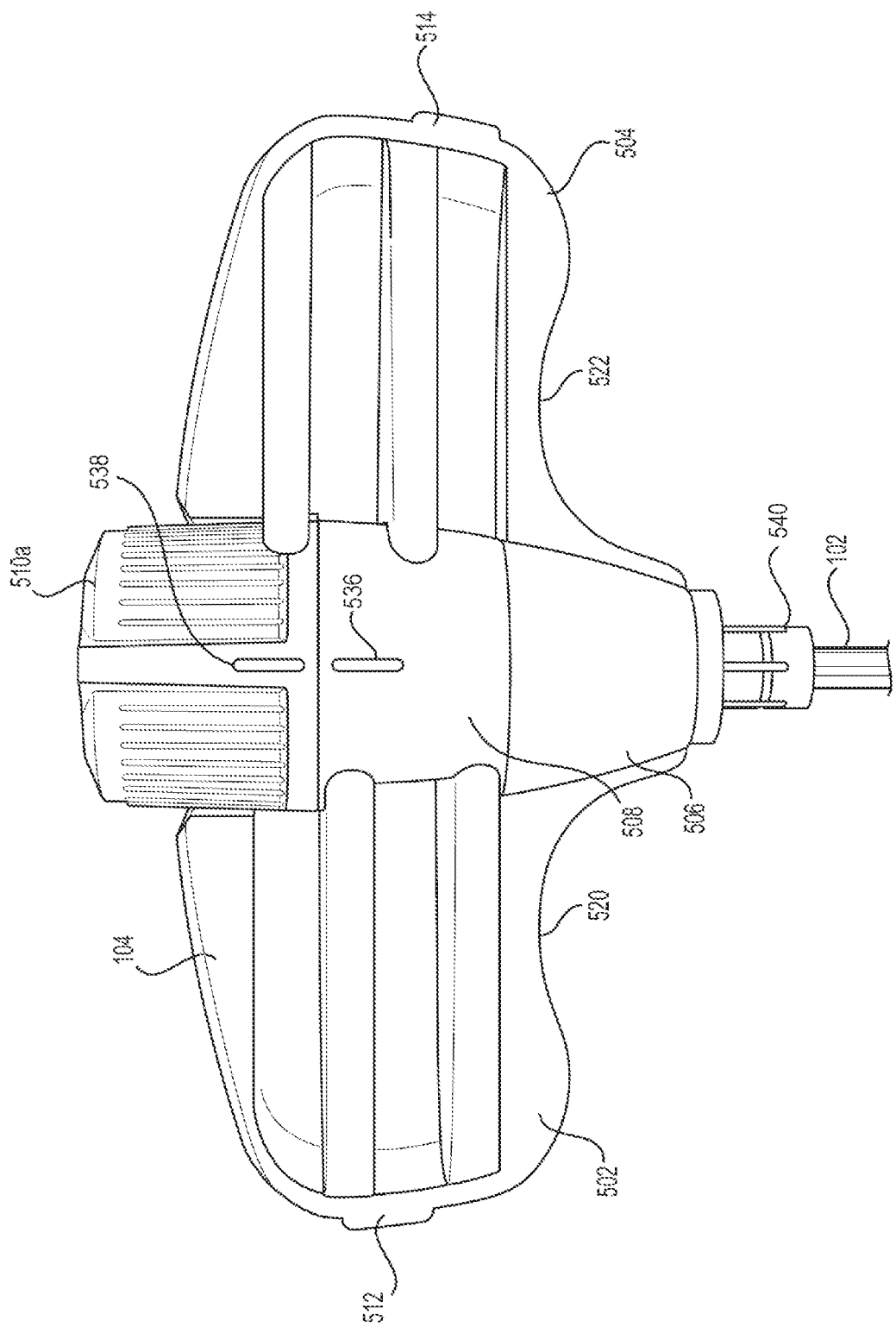

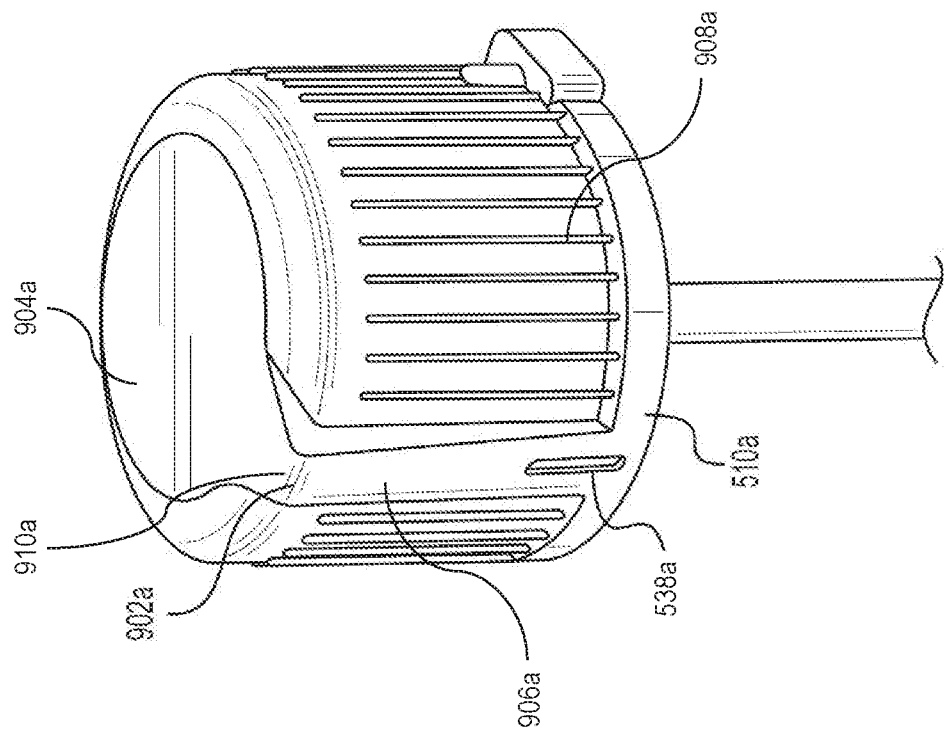
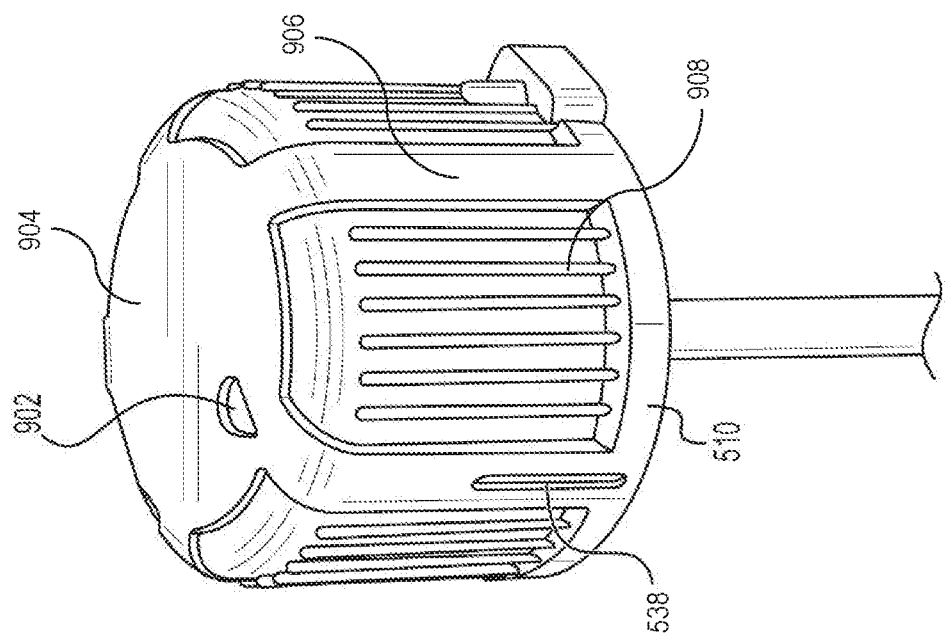
*FIG. 9B*
*FIG. 9A*

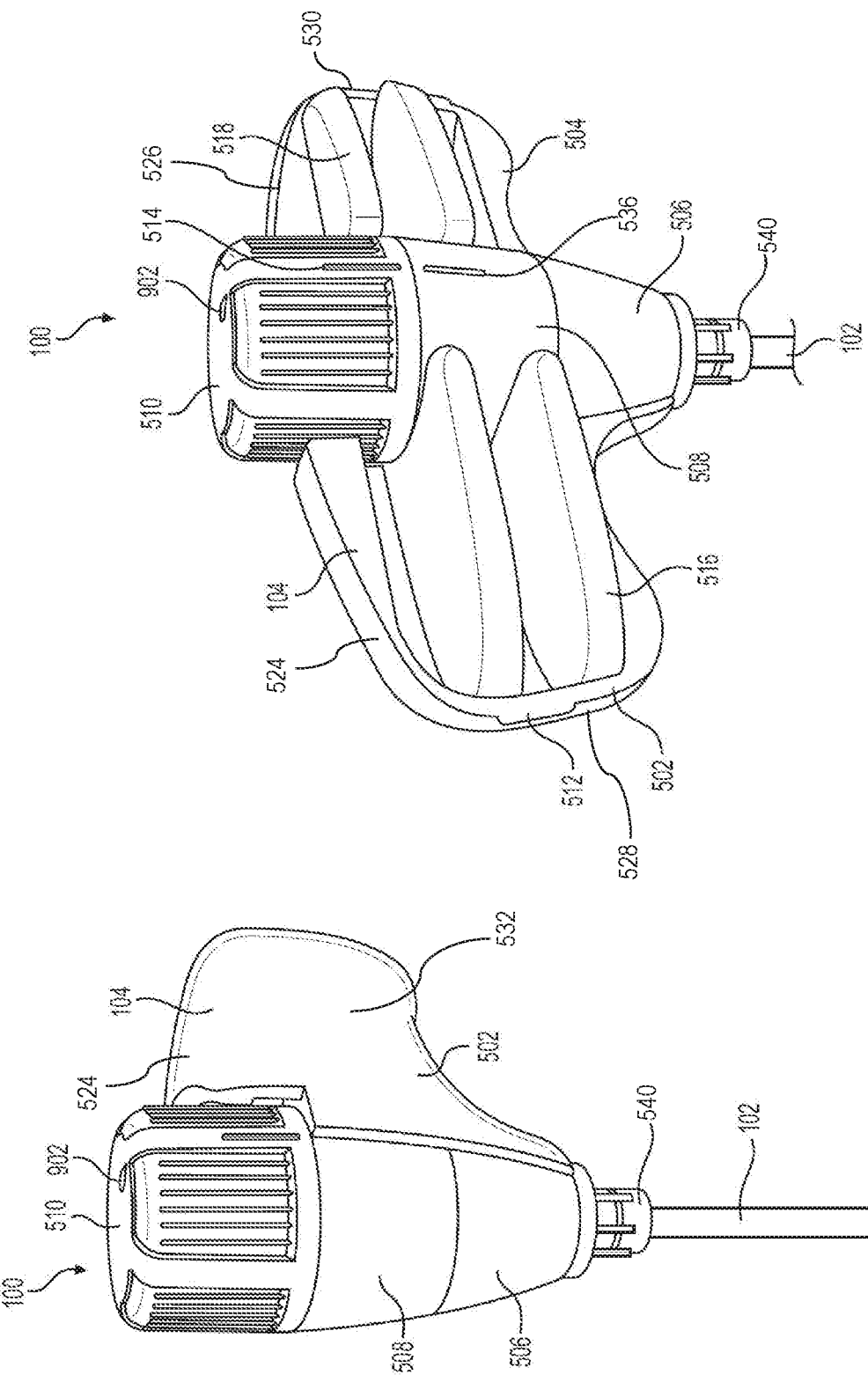

HALF HANDLE BONE ACCESS NEEDLE

CROSS-REFERENCE TO RELATED APPLICATIONS

This application makes reference to U.S. patent application Ser. No. 09/594,167 now U.S. Pat. No. 6,749,595 B1, entitled "CEMENT DELIVEY NEEDLE," filed Jun. 15, 2000. U.S. patent application Ser. No. 11/661,838 now U.S. Pat. No. 8,834,481 B2, entitled "CEMENT DELIVEY NEEDLE," filed Dec. 13, 2007 which is related to U.S. Provisional Patent Application No. 60/608,620 filed Sep. 10, 2004. The entire contents and disclosures of these patent applications are incorporated herein by reference.

BACKGROUND

Field of the Invention

The present disclosure relates to a handle apparatus. More particularly, the handle apparatus may include a surgical needle for expressing bone cement into a vertebral body and used for biopsy and tissue removal.

SUMMARY

According to a first broad aspect, the present disclosure provides a handle device comprising a first wing and a second wing. The first wing and the second wing are configured to pivot about a common axis to one another. The first wing has one or more first ridges, and a first one or more clearance spaces. The second wing has one or more second ridges and a second one or more clearance spaces. The one or more first ridges is configured to be received within the second one or more clearance spaces and the one or more second ridges is configured to be received within the first one or more clearance spaces when the first wing is pivoted about the common axis to the second wing in a folded configuration.

According to a second broad aspect, the present disclosure provides a needle apparatus comprising a handle comprising a first wing, and a second wing wherein the first wing and the second wing are configured to pivot about a common axis to one another. The first wing has one or more first ridges and a first one or more clearance spaces. The second wing has one or more second ridges and a second one or more clearance spaces. The one or more first ridges is configured to be received within the second one or more clearance spaces and the one or more second ridges is configured to be received within the first one or more clearance spaces when the first wing is pivoted about the common axis to the second wing in a folded configuration. A sheath may be connected to the handle. A needle may be disposed through the handle and through the sheath. The apparatus may also include a locking mechanism for retaining the needle to the handle.

According to a third broad aspect, the present disclosure provides a needle apparatus comprising a handle comprising a foldable handle, a sheath connected to the foldable handle, a needle disposed through the foldable handle and through the sheath and a locking mechanism for retaining the needle to the handle.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 8 illustrates a front view of a handle for a needle apparatus according to an alternate embodiment of the present disclosure.

FIG. 9A is a perspective view of a first embodiment of a cap for a needle apparatus according to one embodiment of the present disclosure.

FIG. 9B is a perspective view of a second embodiment of a cap for a needle apparatus according to another embodiment of the present disclosure.

FIG. 11 is a perspective view of the needle apparatus of FIG. 5 with the handle in a completely folded configuration according to one embodiment of the present disclosure.

FIG. 12 is a perspective view of the needle apparatus of FIG. 5 with the handle in a completely unfolded configuration according to one embodiment of the present disclosure.

FIGS. 16A-16L illustrate additional embodiments of alternate handle configurations according to one embodiment of the present disclosure.

DETAILED DESCRIPTION OF THE INVENTION

Definitions

Figure 1:
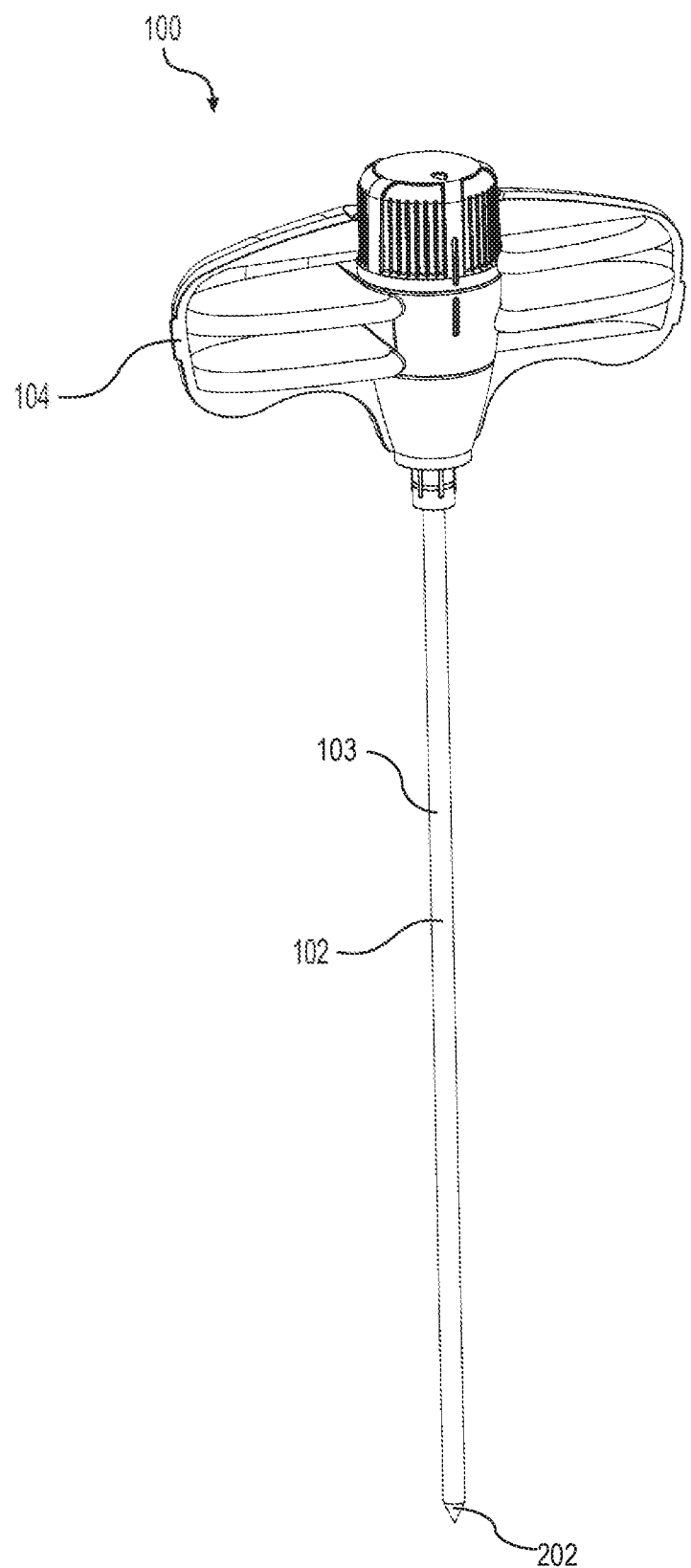
FIG. 1 is a perspective view of a needle apparatus according to one embodiment of the present disclosure.

Where the definition of terms departs from the commonly used meaning of the term, applicant intends to utilize the definitions provided below, unless specifically indicated.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

For purposes of the present disclosure, the term "comprising", the term "having", the term "including," and variations of these words are intended to be open-ended and mean that there may be additional elements other than the listed elements.

For purposes of the present disclosure, directional terms such as "top," "bottom," "upper," "lower," "above," "below," "left," "right," "horizontal," "vertical," "up," "down," etc., are used merely for convenience in describing the various embodiments of the present disclosure. The embodiments of the present disclosure may be oriented in various ways. For example, the diagrams, apparatuses, etc., shown in the drawing FIG.s may be flipped over, rotated by 90° in any direction, reversed, etc.

For purposes of the present disclosure, a value or property is "based" on a particular value, property, the satisfaction of a condition, or other factor, if that value is derived by performing a mathematical calculation or logical decision using that value, property or other factor.

For purposes of the present disclosure, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

For purposes of the present invention, the term "constituent" refers to serving to form, compose, or make up a unit or whole.

For purposes of the present invention, the term "ergonomic" refers to equipment design intended to maximize productivity by reducing operator fatigue and discomfort. Additional aspects include designing and arranging equipment for use so that the user and equipment interact most efficiently, safely and comfortably in the working environment. Ergonomically designed hand tools, for example, may take into account a variety of factors, all geared to minimize muscle injuries, or more specifically injuries of the tendons, joints and nerves that typically occur over time and may affect various body parts, depending on use. In order to avoid, or the very least minimize the risk of injury, ergonomically design hand tools may be designed with consideration of weight, handle, shape and other factors carefully planned for the tool use of the individual.

For purposes of the present invention, the term "foldable" refers to a transitive form of fold meaning to lay one part over another part or to clasp together.

For purposes of the present invention, the term "folded" refers to laying one part over or against another part or to clasp together.

For purposes of the present invention, the term "grip" refers to a part or attachment by which an object is held in the hand.

For purposes of the present invention, the term "handle" refers to a part of, or attachment to, an object that can be moved, held, carried or used by hand. In some embodiments the handle may include an ergonomic design.

For purposes of the present invention, the term "integral" refers to being composed of constituent parts and essential to completeness.

For purposes of the present invention, the term "pistol grip" refers to a handle shaped like the butt of a pistol.

For purposes of the present invention, the term "telescopically" refers to being able to become longer or shorter by having sections that slide inside one another.

DESCRIPTION

While the invention is susceptible to various modifications and alternative forms, specific embodiment thereof has been shown by way of example in the drawings and will be described in detail below. It should be understood, however that it is not intended to limit the invention to the particular forms disclosed, but on the contrary, the invention is to cover all modifications, equivalents, and alternatives falling within the spirit and the scope of the invention.

Intraosseous infusion (IO) is the process of injecting directly into the marrow of a bone. This provides a non-collapsible entry point into the systemic venous system. This technique may be used to provide fluids and medication when intravenous access is not available or not feasible. Intraosseous infusions allow for the administered medications and fluids to go directly into the vascular system. A comparison of intravenous (IV), intramuscular (IM), and intraosseous (IO) routes of administration concluded that the intraosseous route is demonstrably superior to intramuscular and comparable to intravenous administration (in delivering pediatric anesthetic drugs).

Thus, intraosseous infusion is a fast and effective way of getting critical fluids and medications into the vascular system. Whereas intravenous (IV) access uses a peripheral vein, intraosseous infusion (IO) accesses the venous system through the bone marrow. Intraosseous infusion may be considered as a very quick, effective and easy-to-learn skill that can provide rapid vascular access for patients requiring fluids and medications in these circumstances. Rapid vascular access may be required for a variety of medical conditions including, but not limited to, cardiac arrest, cardiac arrhythmias, myocardial infarctions, syncope, hypotension, anaphylactic shock, diabetes and numerous other commonly occurring medical conditions. Generally, any medication or fluid that can be administered by IV can also be administered by IO, with the same quantity and flow rate as IV. Traditionally intravenous infusion (IV), using a peripheral vein, has been the preferred method to establish vascular access. Many studies have demonstrated the numerous downfalls and challenges of solely relying on this technique (IV) for vascular access. IV's, as taught in most class rooms and training programs are usually successful and easy when performed on healthy, well hydrated fellow students. In the "real world" of patient care, especially in an emergency setting, IV's are more difficult to use on patients who are, for example, obese, are hypovolemic, or have poor cardiac output. Studies have demonstrated only 60% to 95% initial success rate for IV attempts. Additionally, the time to start an IV varies from 1.5 to 13 minutes; in most cases significantly longer than the time required to place an IO device.

During in IO procedure, the needle may be injected through the bone's hard cortex and into the soft marrow interior which allows immediate access to the vascular system. The IO needle may be positioned, for example, at a 90 degree angle to the injection site, and the needle is advanced through manual traction, impact driven force, or power driven. Each IO device has different designated insertion locations. The most common site of insertion is the antero-medial aspect of the upper, proximal tibia as it lies just under the skin and is easily located. This is on the upper and inner portion of the tibia. Other insertion sites may include the anterior aspect of the femur, the superior iliac crest, proximal humerus, proximal tibia, distal tibia, sternum (manubrium). An IO infusion can be used on adult or pediatric patients when traditional methods of vascular access are difficult or otherwise cause unwanted delayed management of the administration of medications.

A bone marrow biopsy involves removing a small sample of bone marrow inside bones for testing. Bone marrow is a soft tissue in the center of most large bones. It makes most of the body's blood cells. The biopsy may be performed, for example, utilizing a needle inserted into the bone. In some embodiments, the bone marrow tissue sample (biopsy) may be collected from the top ridge of the back of a hipbone (posterior iliac crest). In another example, the front of the hip may be used. Thus, a biopsy needle may be employed to withdraw a sample of solid bone marrow tissue. The biopsy needle is specially designed to collect a core (e.g., cylindrical sample) of bone marrow.

Percutaneous vertebroplasty involves the injection of a bone cement or suitable biomaterial into a vertebral body via percutaneous route under X-ray guidance. The cement is injected as a semi-liquid substance through a needle that has been passed into the vertebral body, generally along a transpedicular or posterolateral approach. The three main indications are benign osteoporotic fractures, malignant metastatic disease and benign tumors of the bone.

Percutaneous vertebroplasty is intended to provide structural reinforcement of a vertebral body through injection, by a minimally invasive percutaneous approach, of bone cement into the vertebral body. See, for example, Cotton A., et al "Percutaneous vertebroplasty: State of the Art." Radiograhics March-April; 1998, 18(2):311-20; discussion at 320-3. Percutaneous vertebroplasty can result in increased structural integrity, decreased micromotion at the fracture site, and possibly a destruction of pain fibers due to the heat of the bone cement as it polymerizes and sets. Complete pain relief can be achieved in up to eighty percent of patients. As known to those of skill in the art, the cement should have properties that, when injected, can increase vertebral body stiffness and compressive strength. It is generally preferred that the cement is liquid enough to flow into fracture planes and to fuse them. There is some debate about the appropriate thermal properties, but it is believed by some that the heating effect can be beneficial and cause death to local nerve endings involved in pain stimulation. It is generally accepted that most pain relief is achieved due to increased structural integrity.

Generally, when performing vertebroplasty, a needle of an appropriate gauge (such as eight gauge-eighteen gauge (8-18 G) in a smaller vertebral body) is passed down the pedicle until it enters the vertebral body and reaches the junction of the anterior and middle thirds. Great skill is usually required to insert the needle at a suitable angle and pass the needle through the periosteum, down the pedicle and into the vertebral body. In some disclosed embodiments, occasional placement of the needle may occur parapedicular as well. Additionally, the needle may be used in an anterior approach. Also, insertion of the needle generally requires a large applied force. Specifically, a large force can be required, such as when entering the cortex and in the transition from the pedicle to the vertebral body.

A suitable cement is prepared, injected through the needle and into the vertebral body, under lateral X-ray projection fluoroscopy imaging. The injection is stopped as the cement starts to extend into some unwanted location such as the disc space or towards the posterior quarter of the vertebral body, where the risk of epidural venous filling and hence spinal cord compression is greatest. The injection is also discontinued if adequate vertebral filling is achieved.

In many needles of the prior art, there is a step off or change in the angle of the taper at the needle tip. This change in the taper can cause an increase in the required applied force when inserting the needle. The additional applied force can result in a rib fracture. Thus, needles of the prior art can be difficult to insert into the patient. Presently, it is common for a hammer to be used to overcome the force required to insert the needle into the vertebral body.

During insertion of the needle, operator control is reduced due to the greater required applied force. Further, needles are difficult to accurately insert because of the large required applied force.

Prior art needles used in vertebroplasty have certain limitations. Needles such as the MDTECH, bone marrow biopsy/aspiration needle, ref DBMNJ1104T, from Medical Device Technologies, Inc., 3600 S.W. 47.sup.th Avenue, Gainesville, Fla. 32608, have been used for the delivery of bone cement. These needles are designed for obtaining biopsy samples and not for injection of cement. The end of the needles are tapered which can reduce the volume of bone cement injected. On average, about 2 to 5 $cm^3$ of cement can be injected per side. Further, the tip of the needles have a step or a change in the angle of taper, as discussed above, thus making them difficult to insert as resistance is encountered both at the tip and at the step. A large force is required first for the tip to pierce the periosteum and the cortex, and second, a greater force is required for the step of the needle to pass through the periosteum and cortex. Again, additional force is required for the needle tip to pass through the transition from the pedicle to the vertebral body and an even greater force is required for the step of the needle to pass through this transition.

Attempts have been made to employ conventional biopsy needles for the injection of cement, however these needles suffer from certain limitations. For example, many needles are used for retrieving soft-tissue biopsy samples and are not suitable for piercing hard tissue such as bone. Also, many needles do not have an end suitable for attachment of a syringe. Additionally, these needles may not have a handle suitable for applying sufficient force to pierce the cortex or to pass the transition from the pedicle to the vertebral body. Furthermore, for certain prior-art needles having handles wherein multiple instruments are utilized within close proximity to one another, the aforementioned handles may contact and/or impede, hinder or obstruct a nearby instrument as it is manipulated during operation. Such contact or obstruction may interfere with the movement and/or operation of prior-art handle and needle assemblies as they are attempted to be maneuvered during operation. Additional shortcomings of many prior biopsy needles also include having an end with an internal taper that can reduce the volume of cement that can be injected.

Other needles for use in vertebroplasty are disclosed in International publications numbers WO 99/18865 and WO 99/18866. These instruments include a self-tapping, threaded stylet end for tapping into hard tissue. A cannula fits over the stylet and the threaded end is used to draw the cannula into the desired position. A syringe can be attached to the cannula for injection of the cement. The stylet of this needle is rotatably screwed into the desired position. When the stylet is in the desired position, the cannula is rotatably screwed into position. Alternatively, the stylet can be pushed into the desired position or can be positioned by a ratchet assembly and action.

During insertion of these needles, more control can be gained by the slow rotation of the stylet into place, followed by the cannula being moved into place. Therefore, greater time is required to insert this needle than those needles of the prior art. Also, the needle construction is somewhat complex. The screw portion of the stylet can break off in hard bone or can slide on hard bone.

Thus, there exists a need in the art for cement delivery needle which can withstand the rigors of insertion in a patient during percutaneous vertebroplasty and manipulation therein. A need further exists to provide a needle apparatus that could be manipulated around or about other existing equipment during operational use. It would be desirable if such a needle could be readily constructed and readily put into use by those of skill in the art.

The invention of the present disclosure address the short comings of the prior art by providing a cement delivery needle that can withstand the rigors of insertion in a patient during percutaneous vertebroplasty. Disclosed exemplary embodiments provide a handle configured to fold upon itself in order to clear one or more instruments which may be also utilized within a close proximity.

A needle apparatus 100 is shown in FIG. 1. The needle apparatus 100 may be used for expressing a bone cement or a suitable biomaterial into a target site, for example, a vertebral body. By way of example, bone cement materials include, but are not limited to, polymethyl methacrylate (PMMA) and biologically active substances such as calcium triphosphate, calcium phosphate, hydroxyapetite or bone morphogenic protein (BMP). Portions of the needle apparatus 100 may be constructed of surgical grade stainless steel, but other suitable materials, as known to one of skill in the art, that are also compatible with magnetic resonance imaging may be used.

Figure 2A:
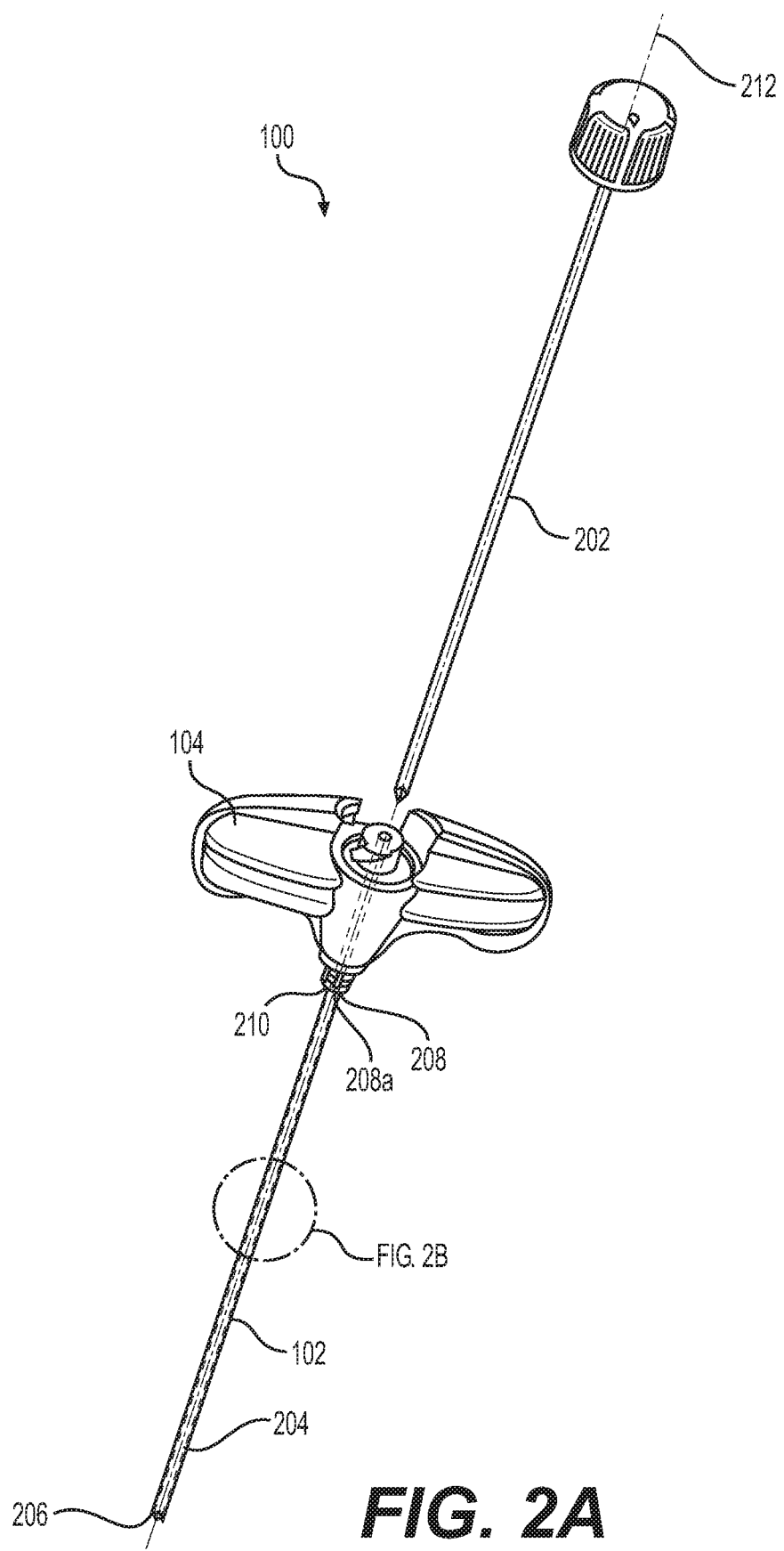
FIG. 2A is a perspective view of an insert removed from elements of the needle apparatus of FIG. 1 according to one embodiment of the present disclosure.
Figure 2B:
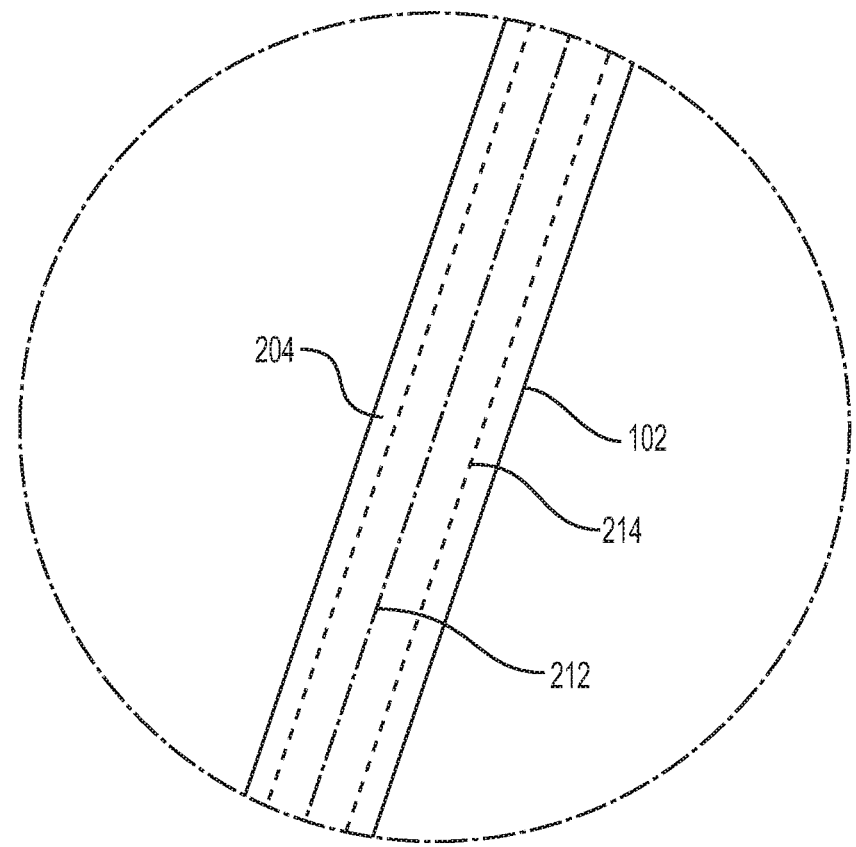
FIG. 2B is an exploded detailed view of a portion of the sheath of FIG. 2A according to one embodiment of the present disclosure.
Figure 3A:
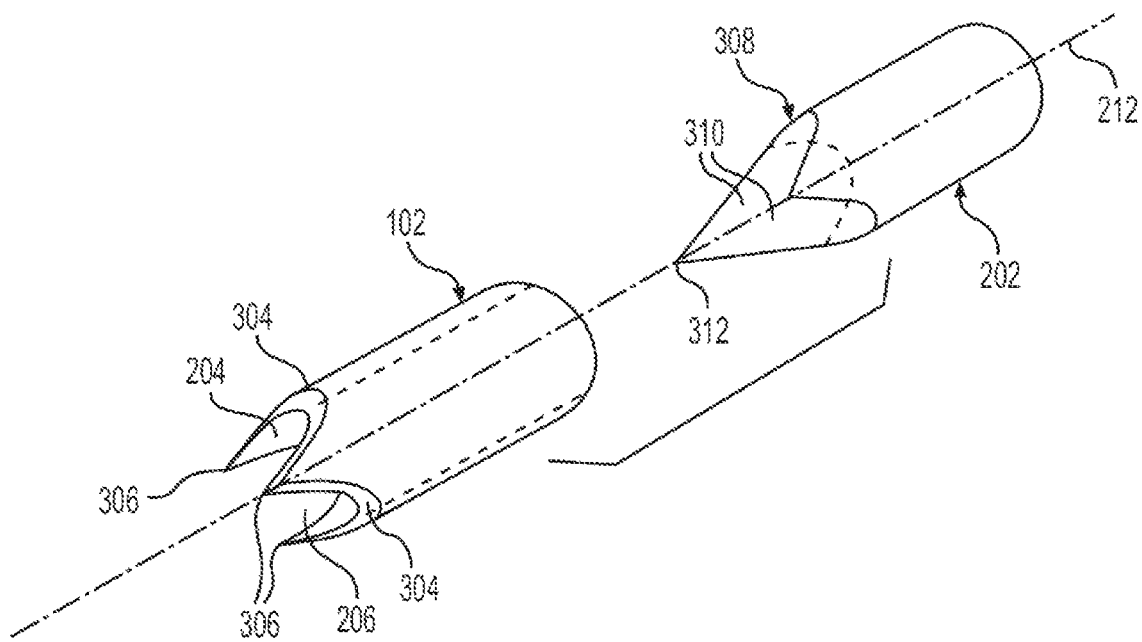
FIG. 3A illustrates a portion of an insert removed from a sheath according to one embodiment of the present disclosure.
Figure 3B:
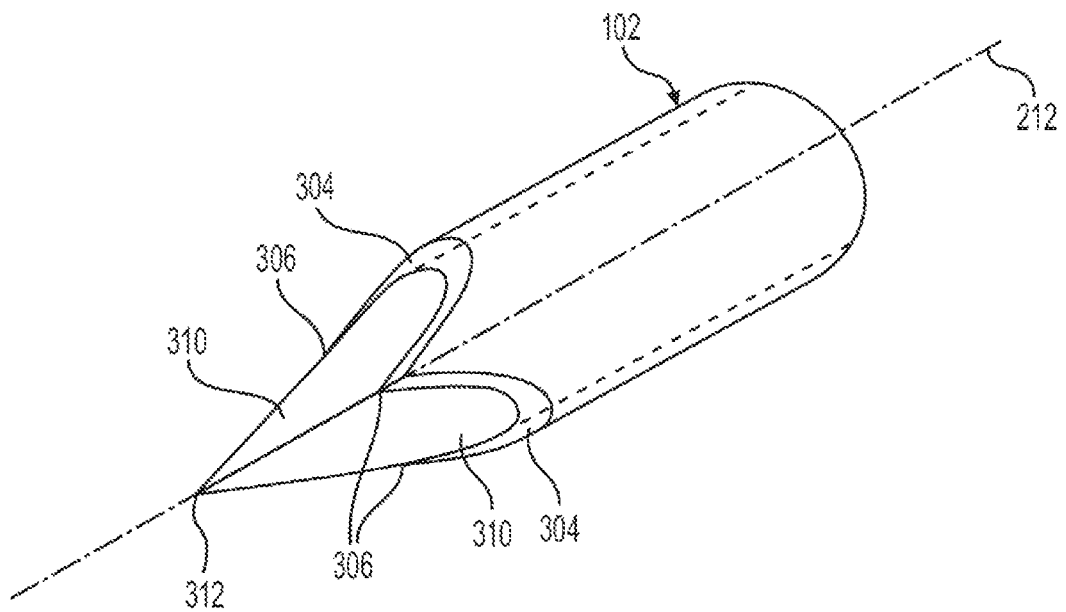
FIG. 3B illustrates the portion the insert of FIG. 3A inserted into the sheath of FIG. 3A according to one embodiment of the present disclosure.

The cement delivery needle apparatus 100 shown in the example of FIG. 1 includes a needle 103 and a handle 104. Needle 103 may comprise a sheath 102 (or cannula) and insert 202 (or stylet). Turning to FIGS. 2A and 2B, insert 202 is receivably removable within a hollow tubular cavity 214 of sheath 102 for insertion of needle apparatus 100, for example, into a vertebral body via a percutaneous route. Insert 202 is removable from the sheath 102 to perform subsequent operations such as to facilitate the injection of cement into a vertebral body.

Referring to FIGS. 1, 2A, 2B, 3A and 3B, sheath 102 is generally a hollow cylinder with an interior 204, an outlet 206 and an inlet 208. The cross-sectional area of interior 204 is not reduced at outlet 206. The diameter of interior 204 may be substantially constant from inlet 208 to outlet 206. In an exemplary embodiment, sheath 102 is cylindrically centered about axis 212 and has three substantially equal, inwardly beveled surfaces 304 defining outlet 206. Each surface 304 is beveled toward axis 212. Thus, sheath 102 has three sharp points 306 at outlet 206. Each sharp point 306 is present at each intersection of two beveled surfaces 304. Each beveled surface 304 is at substantially the same angle to axis 212. Preferably, each beveled surface 304 is at an angle of from about 15° to about 75°. More preferably, each beveled surface 304 is at an angle of from about 30° to about 60°. In some disclosed embodiments, each beveled surface 304 is at an angle of about 45° to axis 212.

Insert 202 is generally cylindrical with a tip 308 and opposing end 210. Tip 308 has three substantially equal, inwardly beveled faces 310. Each face 310 is beveled at substantially the same angle as beveled surfaces 304. Thus, all three beveled faces 310 intersect at a leading point 312 that protrudes from sheath 102 upon insertion. When insert 202 is received within sheath 102, insert 202 can be oriented such that each of beveled faces 310 is aligned with one of beveled surfaces 304. The bevel angle is substantially identical between insert 202 and sheath 102. Thus there is no step from tip 308 to sheath 102 thereby presenting three generally continuous beveled faces from sheath 102 to tip 308 of insert 202. The surfaces of beveled faces 310 may be oriented to form a generally smooth transition to the surfaces of beveled surfaces 304 during an alignment as discussed below.

Figure 4A:
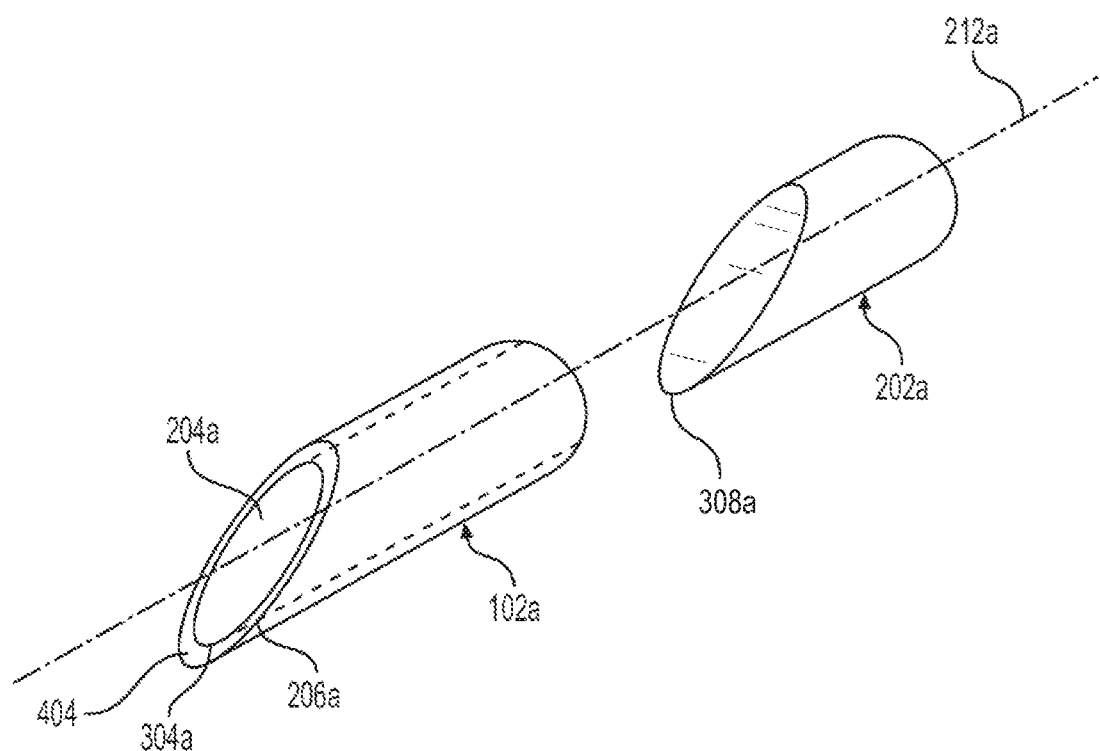
FIG. 4A illustrates a portion of an insert removed from a sheath according to an alternate embodiment of the present disclosure.
Figure 4B:
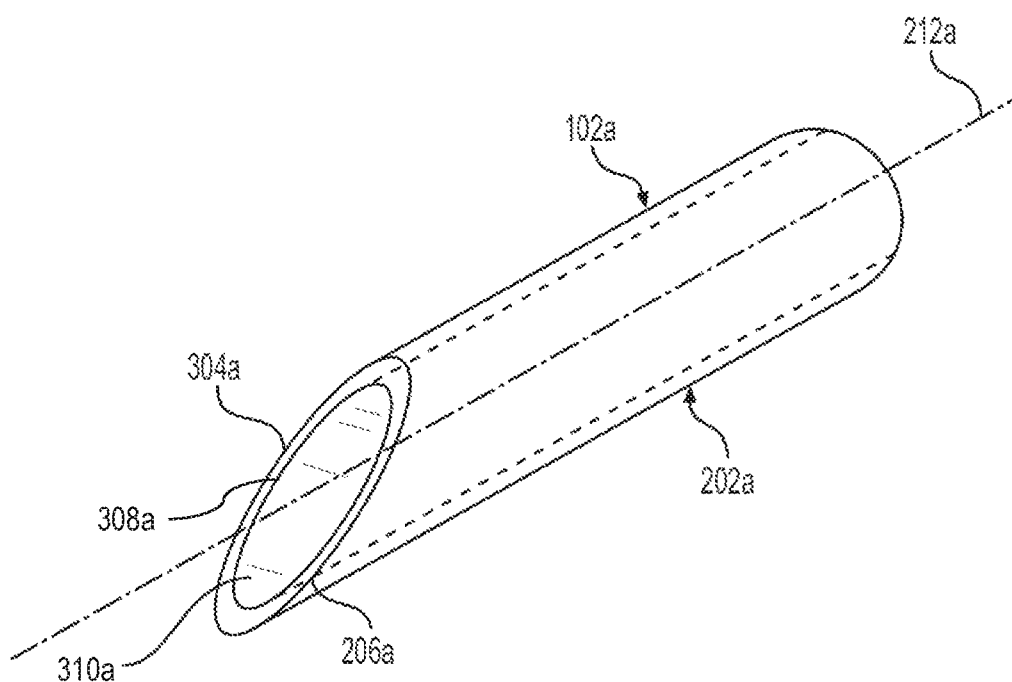
FIG. 4B illustrates the portion the insert of FIG. 4A inserted into the sheath of FIG. 4A according to an alternate embodiment of the present disclosure.

FIGS. 4A and 4B illustrate an alternative insert 202a and sheath 102a similar to the insert 202 and sheath 102 described above and given the same numeral with the suffix a. Sheath 102a is generally a hollow cylinder with an interior 204a, an outlet 206a and an inlet 208a (similar to inlet 208 of sheath 102). Sheath 102a is cylindrically centered about an axis 212a. In a disclosed embodiment, the cross-sectional area of interior 204a is not reduced at outlet 206a. Thus, the diameter of interior 204a, is substantially constant from inlet 208a to outlet 206a. Outlet 206a is beveled such that it presents a single planar face 304a. It is believed that planar face 304a can be at an angle of from about 15° to about 75° to axis 212a. Planar face 304a can also be at an angle of from about 30° to about 60° to axis 212a. It will be understood by those of skill in the art, however, that planar face 304a can be at any suitable, desired angle. In the disclosed embodiment, planar face 304a of sheath 102a defines a leading edge 404. As in the first embodiment, inlet 208a is fixed to a handle 104 for grasping by the operator. Handle in the present embodiment can be the same as handle 104 in the first embodiment.

Insert 202a is generally cylindrical with a tip 308a. Tip 308a is beveled at substantially the same angle as outlet 206a of sheath 102a creating beveled face 310a. Thus, when insert 202a is received within sheath 102a, insert 202a can be oriented such that tip 308a is flush with outlet 206a. Planar face 304a is aligned with beveled face 310a. The bevel angle is substantially identical between insert 202a and sheath 102a, thus there is no step from tip 308a to outlet 206a. Inlet 208 (or 208a) may be fixed to a handle 104 for grasping by the operator. Inlet 208 (or 208a) can be fixed to handle 104 by friction fit or other means as will occur to those of skill in the art. Opposing end of insert in the disclosed embodiment can be the same as opposing end of insert in the first embodiment. Other features of the present embodiment of needle not outlined herein can be the same as those features of the first embodiment of needle.

Referring to FIGS. 5-13, handle 104 can be any shape suitable for grasping by an operator. According to one disclosed embodiment, handle 104 may be configured having a plurality of wings for grasping. Thus, in one exemplary embodiment, a first wing 502 and a second wing 504 is provided. The second wing 504 may be configured in a symmetrically opposite direction to the first wing 502, for example, about axis 212. First wing 502 and second wing 504 may each be provided with one or more first ridges 516 and one or more second ridges 518, respectively, for providing rigidity and support to each respective wing 502, 504. In one embodiment the one or more first ridges 516 is configured on an interior side 550 of first wing 502 and one or more second ridges 518 is configured on an interior side 552 of second wing 504. A side of each first wing 502 and second wing 504 may include tabs 512, 514, respectively. The position of each tab 512, 514 may be vertically offset from one another along each respective side of first wing 502 and second wing 504.

Components of handle 104 may comprise a molded polymer but other materials and forming processes can be used. In one disclosed embodiment, handle materials may include ABS (Acrylonitrile Butadiene Styrene). Characteristics of employed ABS materials may comprise the following properties/characteristics:

|  | Value | Unit | Test Standard |
|---|---|---|---|
| Processing/Physical Characteristics | | | |
| ASTM Data | | | |
| Melt Flow Index | 5.6 | g/10 min | ASTM D 1238 |
| Temperature | 230 | ° C. | — |
| Load | 3.8 | kg | — |
| Density | 1050 | kg/m³ | ASTM D 792 |
| Rheological properties | | | |
| ISO Data | | | |
| Melt flow index, MFI | 19 | g/10 min | ISO 1133 |
| MFI temperature | 220 | ° C. | — |
| MFI load | 10 | kg | — |
| Mechanical Properties | | | |
| ISO Data | | | |
| Tensile Modulus | 2530 | MPa | ISO 527-1/-2 |
| Flexural modulus, 23° C. | 2410 | MPa | ISO 178 |
| Izod Impact notched, 23° C. | 23 | kJ/m² | ISO 180/1A |
| Izod Impact notched | 8 | kJ/m² | ISO 180/1A |
| Temperature | −30 | ° C. | — |
| ASTM Data | | | |
| Tensile Modulus | 2268 | MPa | ASTM D 638 |
| Tensile Strength at Yield | 43.4 | MPa | ASTM D 638 |
| Tensile Strength at Break | 33.1 | MPa | ASTM D 638 |
| Elongation at Yield | 2 | % | ASTM D 638 |
| Elongation at Break | 24 | % | ASTM D 638 |
| Flexural Modulus | 2337 | MPa | ASTM D 790 |
| Izod Impact notched, ⅛ in | 0.32 | kJ/m | ASTM D 256 |
| Izod Impact notched, Low-Temperature | 0.133 | kJ/m | ASTM D 256 |
| Temperature | −30 | ° C. | — |
| Thermal Properties | | | |

|  | Value | Unit | Test Standard |
|---|---|---|---|
| ISO Data | | | |
| Temp. of deflection under load, 1.80 MPa | 80 | ° C. | ISO 75-1/-2 |
| Vicat softening temperature, 50° C./h 50 N | 100 | ° C. | ISO 306 |
| Coeff. of linear therm. expansion parallel | 88.2 | E-6/K | ISO 11359-1/-2 |
| Coeff. of linear therm. expansion, normal | 88.2 | E-6/K | ISO 11359-1/-2 |
| ASTM Data | | | |
| DTUL @ 66 psi | 94 | ° C. | ASTM D 648 |
| DTUL @ 264 psi | 80 | ° C. | ASTM D 648 |
| Vicat Temperature | 97.8 | ° C. | ASTM D 1525 |
| Other Properties | | | |
| ISO Data | | | |
| Density | 1050 | kg/m³ | ISO 1183 |
| Process Recommendation Injection Molding | | | |
| Pre-drying - Temperature | 80-95 | ° C. | — |
| Pre-drying - Time | 2-4 | h | — |
| Processing humidity | ≤0.1 | % | — |
| Melt temperature | 220-260 | ° C. | — |
| Mold temperature | 50-70 | ° C. | — |
| Zone 1 | 190-210 | ° C. | — |
| Zone 2 | 205-225 | ° C. | — |
| Zone 3 | 215-240 | ° C. | — |
| Nozzle temperature | 220-260 | ° C. | — |
| Screw speed | 30-60 | rpm | — |
| Back pressure | 0.3-0.7 | MPa | — |
| Characteristics | | | |
| Processing | | | |
| Injection Molding | | | |
| Chemical Resistance | | | |
| Radiation Resistance | | | |
| Certifications | | | |
| Food contact, Food approval FDA 21 CPR | | | |
| Applications | | | |
| General Purpose, Medical | | | |

The overall handle design and configuration may be ergonomically adapted to more easily fit within the hand of a user, provide increased dexterity and to prohibit fatigue during use. For example, ergonomic finger indentations 520, 522 may be provided along an underside of first wing 502 and second wing 504, respectively. A side profile of ridges 516, 518 may be rounded (e.g., see FIG. 12) to more easily conform to a user's palm for secure handling of handle 104. The disclosed side profile of ridges 516, 518 facilitate the ergonomic design thereby providing support in the hand of a user. In addition, profiles of exterior top surfaces 524, 526, exterior side surfaces 528, 530, and exterior rear surfaces 532, 534 of first wing 502 and second wing 504, respectively, may also include a generally rounded surface edge configuration to contribute to the ergonomic design and feel of handle 104.

In one disclosed embodiment, handle 104 is comprised of multiple pieces including a first connector 506, a second connector 508 and a third connector or cap piece 510. Second connector 508 and cap piece 510 may include respective alignment indicator marks 536 and 538 to provide an alignment feature of handle 104. Each component of the first connector 506 and second connector 508 and cap piece 510 may be aligned to fit together axially, for example along axis 212. In addition, first connector 506 and second connector 508 may be telescopically engaged along axis 212. As evidenced, for example, in FIG. 15, first connector 506 may be integrally formed with second wing 504. Second connector 508 may be integrally formed with first wing 502. Thus, integrally formed first connector 506 and second wing 504 is configured in a telescopic assembly with integrally formed second connector 508 and first wing 502. Retainer mechanism 540 may be employed provided, for example, against first connector 506 to retain a sheath/needle covering (not shown).

Figure 6:
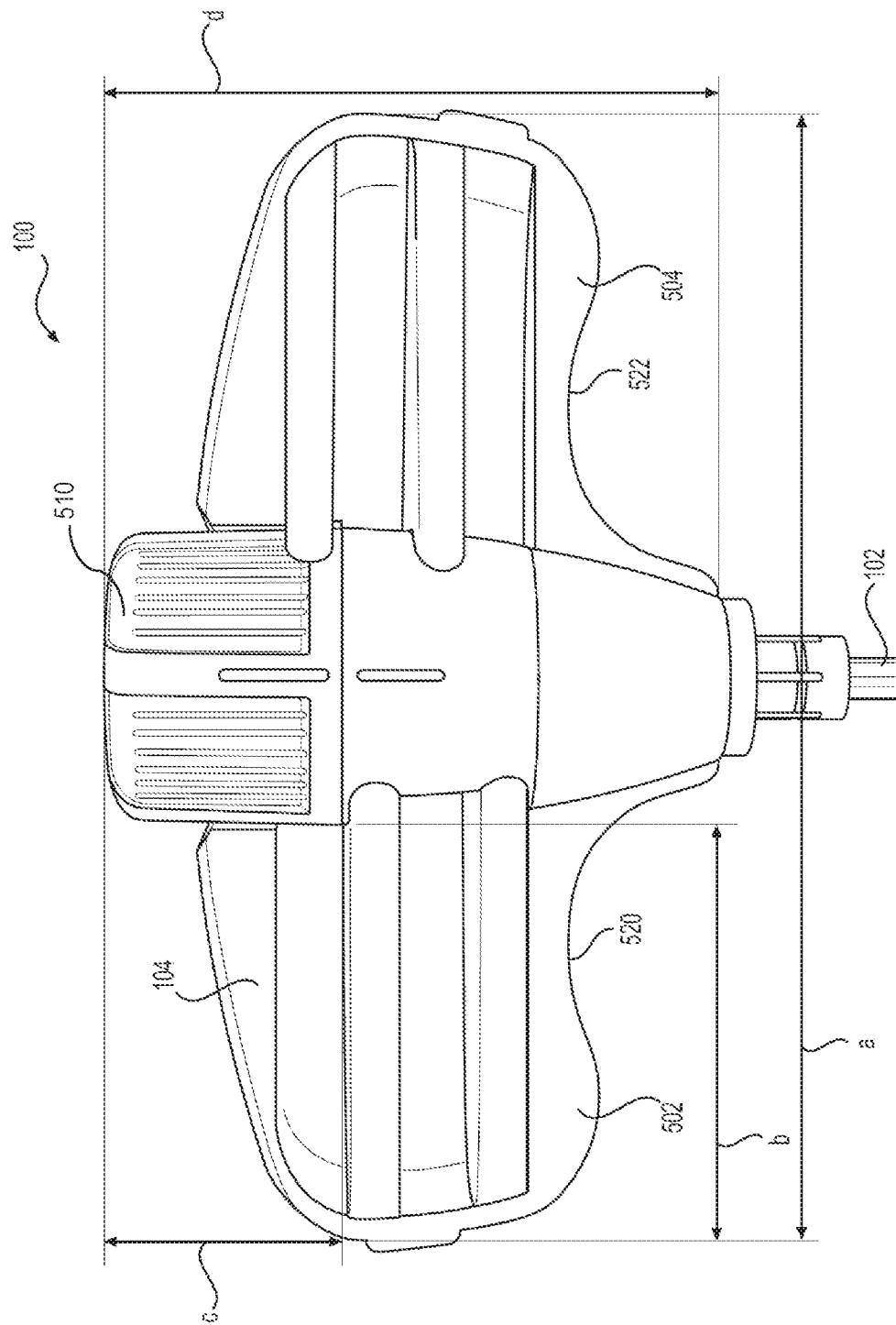
FIG. 6 illustrates exemplary dimensions of the handle of FIG. 5 according to one embodiment of the present disclosure.
Figure 7:
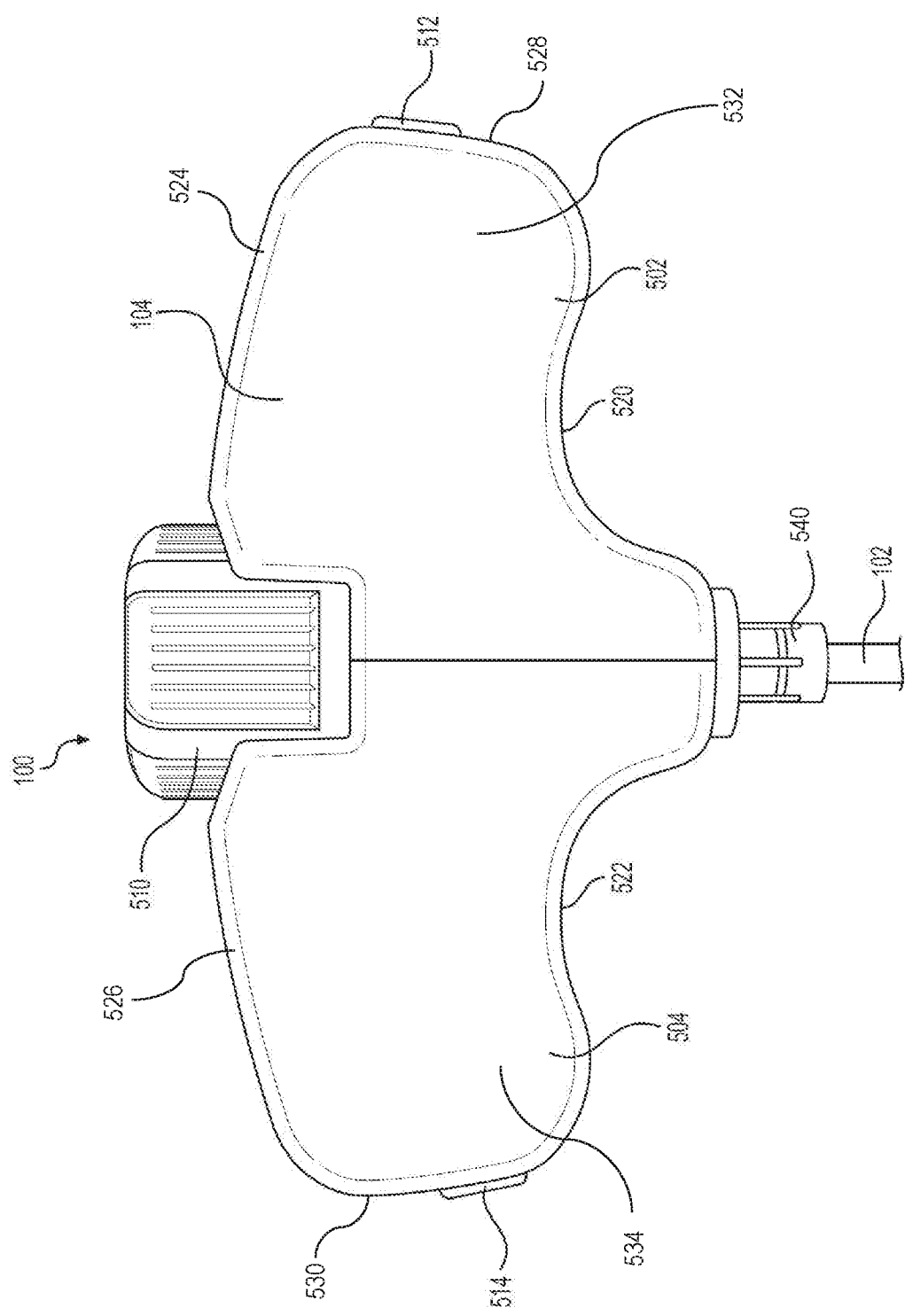
FIG. 7 illustrates a rear view of the handle of FIG. 5 according to one embodiment of the present disclosure.

Turning to FIG. 6, handle 104 may be appropriately dimensioned to facilitate the ergonomic design of the disclosed invention. In one embodiment a complete wingspan of wings 502, 504 is approximately 2.96 inches. Each handle length b of wings 502, 504 is approximately 1.08 inches. A height c of cap piece 510 may be approximately 0.625 inches. An overall height d of handle 104 is approximately 1.6 inches. While one or more dimensions may change, it is important that handle 104 is naturally and ergonomically captured as it is received in the palm of a user's hand for handling and maneuvering.

Figure 10:
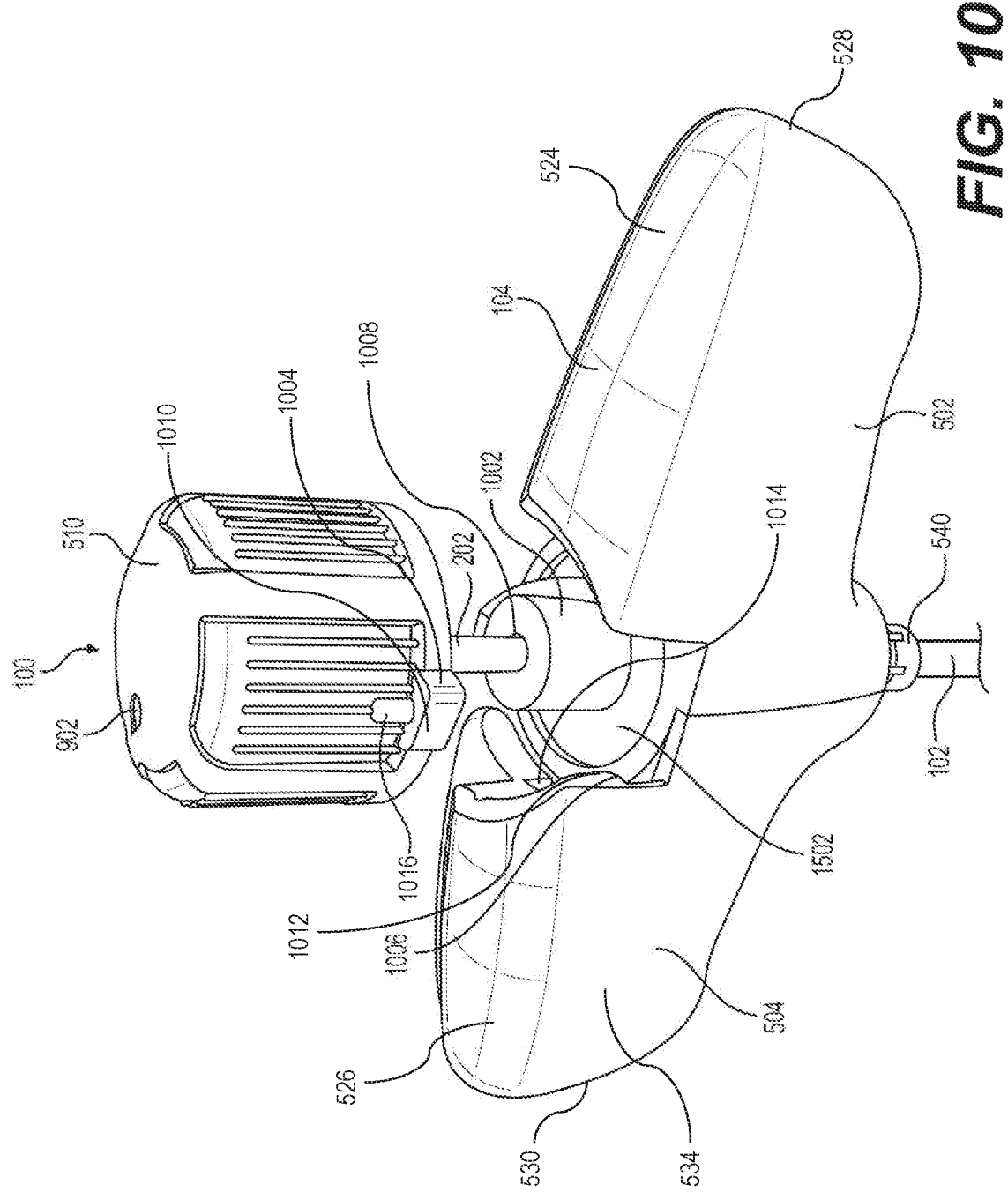
FIG. 10 illustrates a cap and insert partially assembled to a needle apparatus according to one embodiment of the present disclosure.
Figure 14:
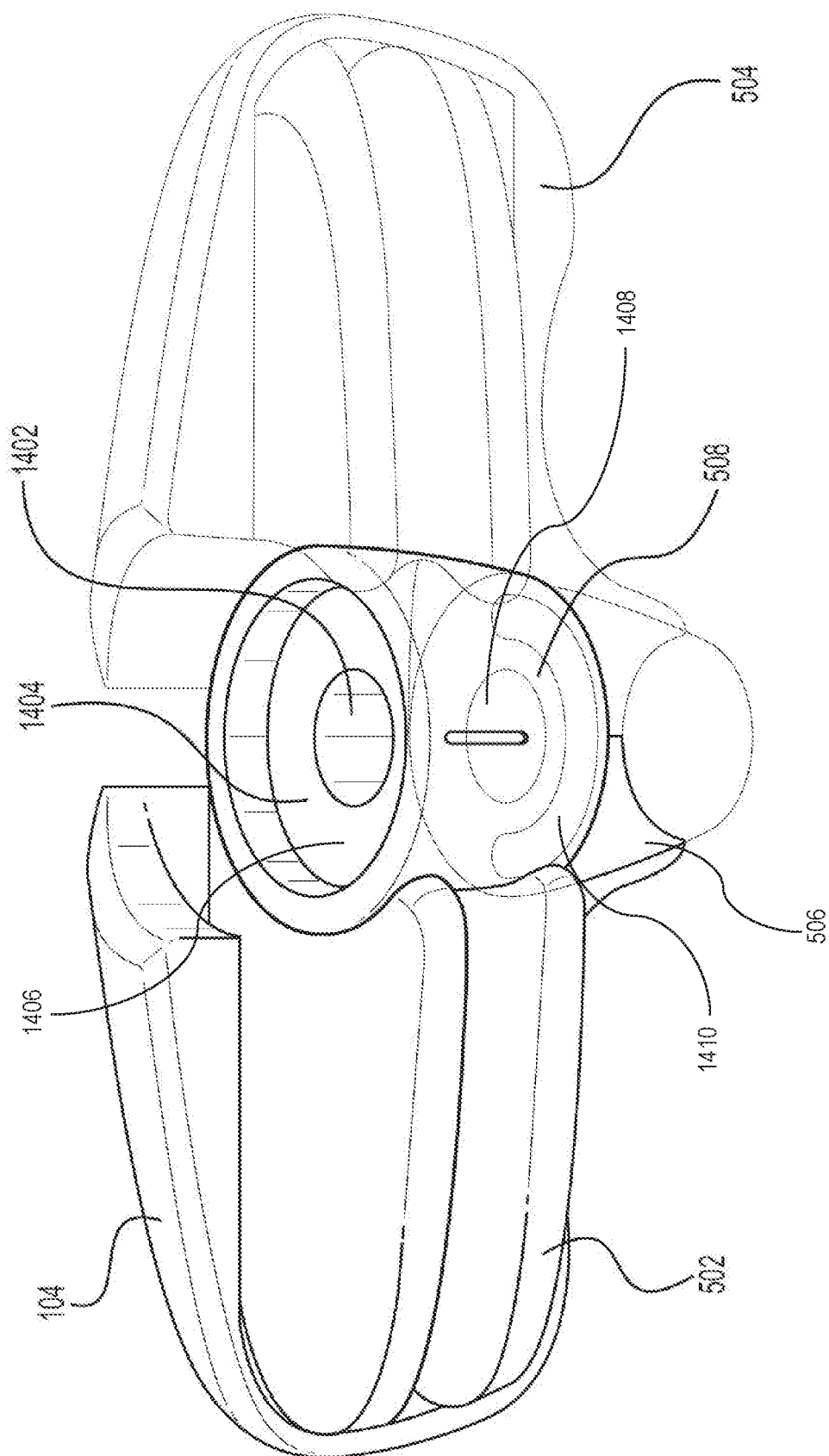
FIG. 14 illustrates an internal partial configuration of a handle according to one embodiment of the present disclosure.
Figure 15:
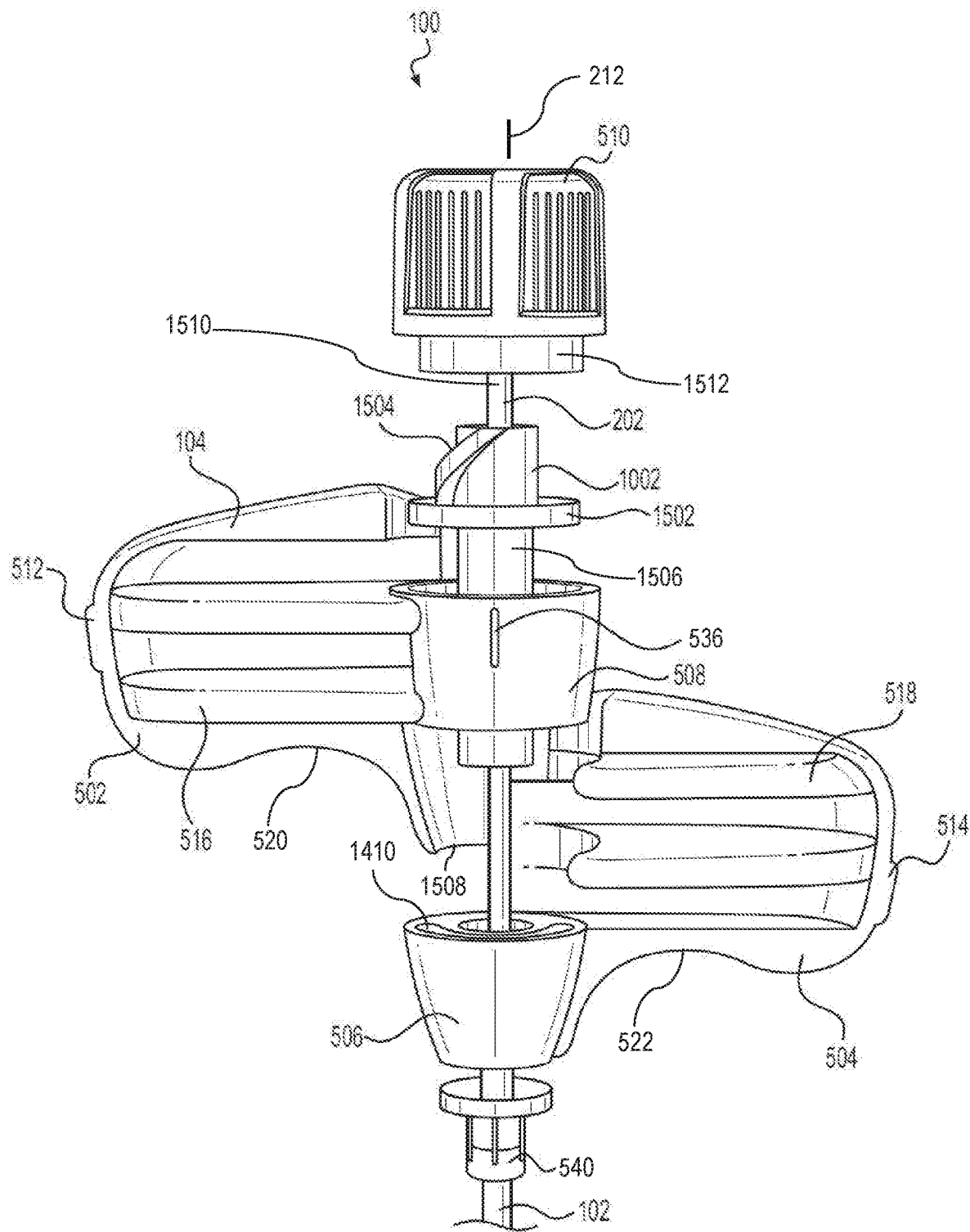
FIG. 15 illustrates the assembly of components for a handle configuration according to one embodiment of the present disclosure.
Figure 16A:
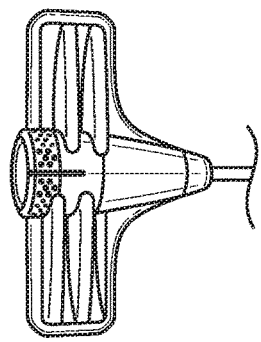
Figure 16B:
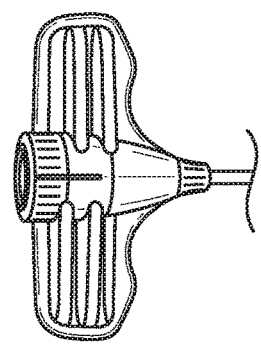
Figure 16E:
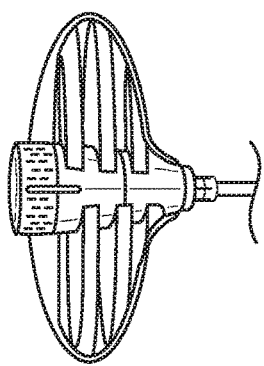
Figure 16D:
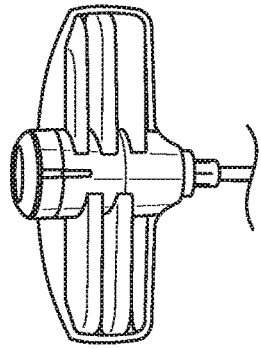
Figure 16G:
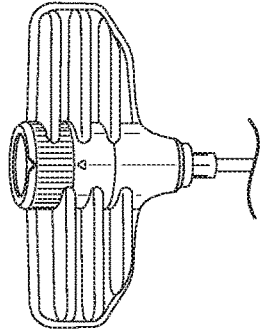
Figure 16F:
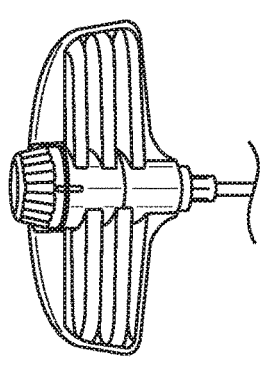
Figure 16H:
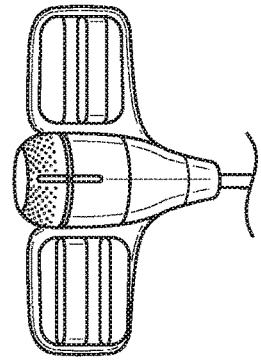
Figure 16K:
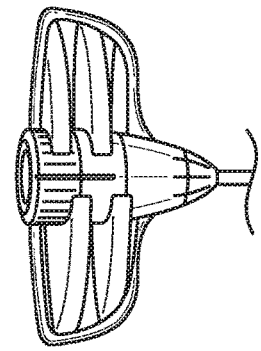
Figure 16J:
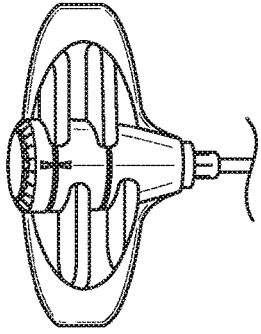
Figure 16I:
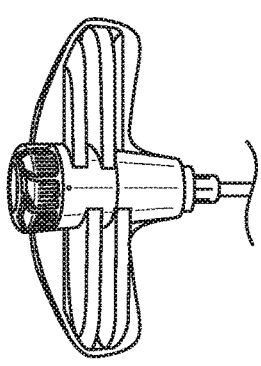

As illustrated in FIGS. 10, 14 and 15, second connector 508 may include a luer connector 1002 disposed and retained, for example, in an internal recess 1404 thereof. Luer connector 1002 has an externally threaded center post 1504. Third connector or cap piece 510 can be any connector that is releasably attached with second connector 508 of handle 104. In one disclosed configuration, third connector or cap piece 510 is a female luer connector. Accordingly, third connector or cap piece 510 may be retained to luer connector 1002 of second connector 508, for example, by providing corresponding mated thread receptacles for receiving complimentary threads of center post 1504 when assembled, for example, by twisting cap 510 onto the threads in a mated engagement. Thus, third connector or cap piece 510 may be internally threaded to receive complimentary external threaded center post 1504 when insert 202 is received within sheath 102. In some disclosed embodiments, cap piece 510 may include a threaded 180 degree twist cap insert 1512. A locking mechanism may be provided to retain insert 202 within sheath. In some embodiments, the locking mechanism may include locking the insert 202 to handle 104. In the disclosed invention, third connector or cap piece 510 and luer connector 1002 are a luer lock and may serve as a locking mechanism; however, it will be understood by those skilled in the art that third connector or cap piece 510 and luer connector 1002 can be any releasable attachment suitable for connecting sheath 102 and insert 202.

An injector may also be releasably attachable with luer connector 1002. The injector can be any part suitable for cement delivery through sheath 102 and into vertebral body, for example. In an exemplary illustration, the injector can be a syringe such as the Medallion Syringe from Merit Medical Systems Inc., South Jordan Utah, 84095 U.S.A. Other suitable injectors may be used such as the Dyna Torque Injector from Parallax Medical, Inc., 455 Ravendale Dr., Suite B, Mountain View Calif., 94043, the "Duro-Ject" and "Osteo-force Injector" injector systems from IZI as will occur to those of skill in the art. The syringe can contain cement for injection into inlet 208, 208a through sheath 102 and into a vertebral body.

The disclosed needle apparatus 100 can be 10, 11, 13, or 14 gauge. Generally, 10 or 11 gauge needles are used for delivery of cement to a vertebral body in a lumbar or sacral vertebra and 13 or 14 gauge needles are used for delivery of cement to a vertebral body in a thoracic or cervical vertebra.

Preferably, needle apparatus 100 is from about eight cm to about twenty cm in length. More preferably, needle apparatus 100 is from about ten cm to about fifteen cm in length. It will be understood by those skilled in the art, however, that the size and proportions of needle apparatus 100 may vary depending on the vertebral body being filled and the subject.

Turning to FIG. 15 threaded center post 1504 may include a bottom portion 1506 that is configured to be received within and through hollow mating interior 1402 of second connector 508. Both the bottom portion 1506 and the interior 1402 may comprise a complimentary cylindrical configuration and appropriately dimensioned for the interior 1402 to receive the bottom portion 1506 when assembled. In one disclosed embodiment, threaded center post 1504 comprises a flanged portion 1502 that is configured to rest upon a corresponding contact surface 1406 of an internal recess 1404. Internal recess 1404 and corresponding contact surface 1406 may be appropriately dimensioned to receive flanged portion 1502 of threaded center post 1504 to provide secure retention thereof.

Bottom portion 1506 may be appropriately dimensioned to extend through interior 1402 of second connector 508 and into a hollow interior 1408 of first connector 506. Both the bottom portion 1506 and the interior 1408 may comprise a cylindrical configuration and appropriately dimensioned for the interior 1408 to receive the bottom portion 1506. In a final assembly, luer connector 1002 includes a hollow interior cavity 1008 (FIG. 10) that is aligned with, and extends from interior 204 thus presenting a continuous concentric cylindrical hollow cavity from handle 104 to outlet 206. Opposing end 1510 of insert 202 may be fixed to cap piece 510. Hence, interior cavity 1008 provides for receiving insert 202 there through such that insert 202 extends through both first connector 506 and second connector 508 into interior 204 of sheath 102 Interior cavity 1008, interior 1402, and interior 204 may comprise concentric hollow cavities about axis 212 for accommodating insert 202 there through.

Once insert 202 is disposed within sheath 102, cap piece 510 may be secured to handle 104 by twisting cap piece 510 onto threaded center post 1504 to secure insert 202 within sheath 102. In one disclosed embodiment, as shown in FIG. 10, a locking mechanism may be employed on handle 104 comprising, for example, a locking tab 1004 that is disposed within receiving sleeve 1006. Thus, in an exemplary configuration, locking tab 1004 may be formed as a pronounced surface button structure 1016 and a guide surface structure 1010 formed generally along an external side of the bottom rim of cap piece 510. In select embodiments, receiving sleeve 1006 may be formed in an internal portion of second wing 504 and appropriately positioned and dimensioned to receive guide surface structure 1010 when cap piece 510 is twisted onto threaded center post 1504. During twisting, pronounced surface button structure 1016 may contact and move along internal contact surface 1012 of second wing 504 and eventually rest within an internal stop groove 1014 of second wing 504. Disclosed embodiments may include an audible "snap" or click feature to facilitate a user's determining when cap piece 510 is secured to handle 104 along center post 1504 and also for determining alignment of beveled faces with surfaces of beveled surfaces 304, as discussed below. For example, an audible sound feature may be employed such that of an audible "snap" sound may be heard or a click may be felt during contact of pronounced surface button structure 1016 as it moves into contact and along internal contact surface 1012 of second wing 504 and eventually rests within internal stop groove 1014 of second wing 504. Pronounced surface button structure 1016 may be retained within internal stop groove 1014, for example, by friction fit/contact to obtain a secured and locked connection of cap piece 510 to handle 104. Thus, upon inserting insert 202 within sleeve 102, insert 202 is locked within sheath 102 when cap piece 510 is secured and locked to handle 104, as described herein. In the secured and locked configuration, disclosed embodiments provide alignment of alignment indicator marks 536 and 538 thereby indicating that the surfaces of beveled faces 310 are oriented to form a generally smooth transition to the surfaces of beveled surfaces 304.

Turning to FIGS. 9A and 9B a first and second embodiment of cap piece 510, 510*a*, respectively, is illustrated to demonstrate alternative designs for indicator marks 538, 538*a*. In addition, a visual indicator mark may be disposed at a top 904, 904*a* of cap piece 510, 510*a*. In one embodiment a depressed indicator mark 902 is formed in top 904. In another embodiment, a pronounced ridge 902*a* is formed along a ridge stemming from the top 904*a* and transitioning to a side 906*a* of cap piece 510*a*. Top 904, 904*a* of cap piece 510, 510*a* is generally raised above exterior top surfaces 524, 526 of first and second wings 502, 504, respectively, and flat and sufficiently sized and strengthened to serve as a striking area. The striking area may be presented to support receiving striking blows to top 904, 904*a* by another striking instrument (such as a hammer) that may be employed by a user, for example, during a surgical procedure. The aforementioned raised feature increases more accurate striking of top 904, 904*a* such that first and second wings 502, 504 are less likely to be struck which may, in turn, alter the positioning of needle apparatus 100 and handle 104. Pronounced ridge 902*a* may provide an increased generally flat striking surface area 910*a* such that a striking tool is less prone to slide off the top 904*a* and possibly hitting the side 906*a* of cap piece 510*a*. This inadvertent action could unfavorably misalign the angle of an inserted needle of needle apparatus 100 during a procedure.

Figure 5:
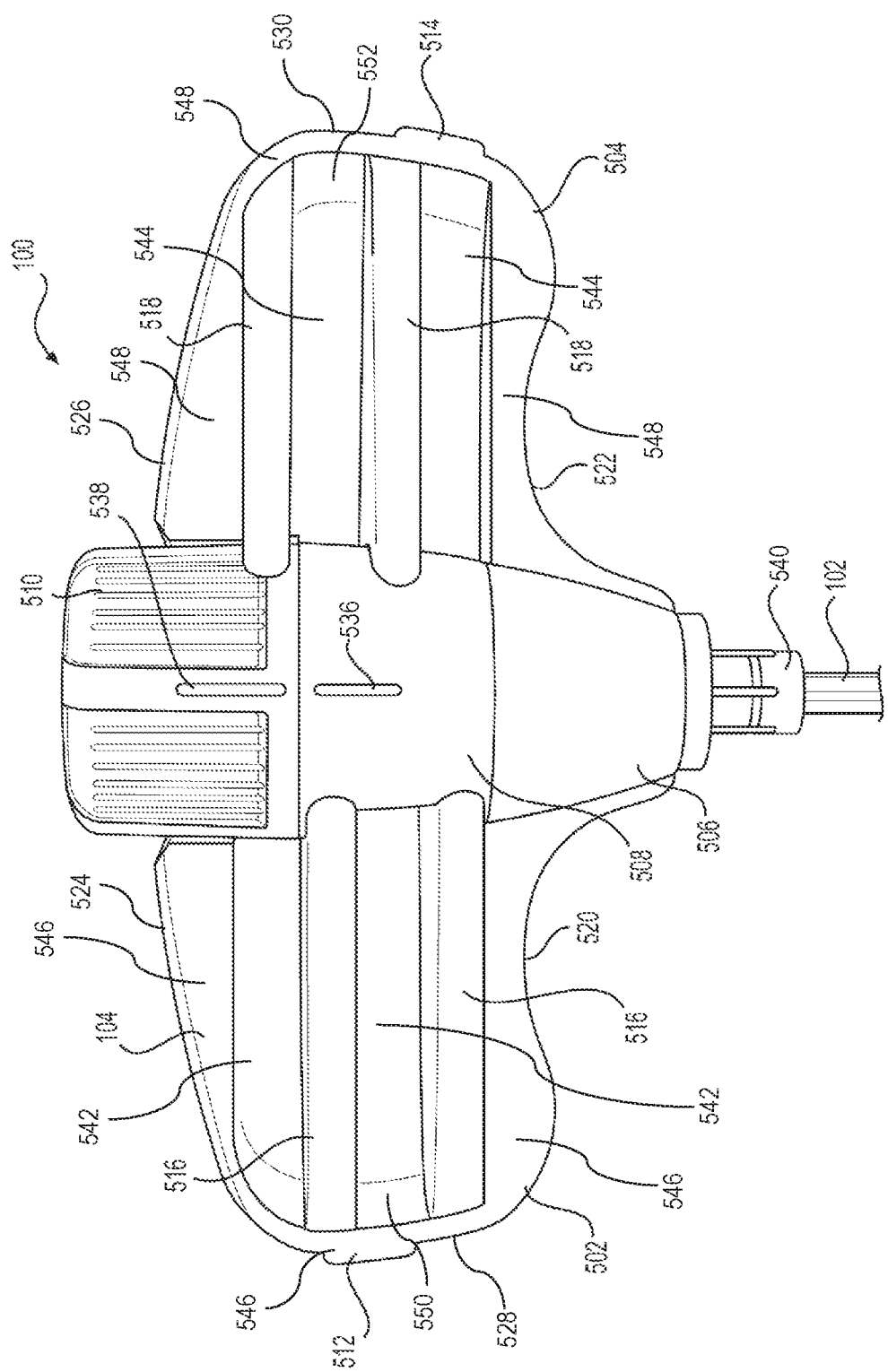
FIG. 5 illustrates a front view of a handle for a needle apparatus according to one embodiment of the present disclosure.

Cap piece 510, 510*a*, may include ridge lines 908, 908*a* along its sides 906, 906*a*, respectively. Ridge lines 908, 908*a* may be configured as tactile surface projections or indentations for facilitating handling of cap piece 510, 510*a* by a user. In all instances, indicator marks 538, 538*a*, depressed indicator mark 902, pronounced ridge 902*a*, and ridge lines 908, 908*a*, alone or in combination with indicator mark 536, serve as visual and/or tactile indicators to a user operating handle 104, for example, for operational and alignment purpose(s). According to disclosed embodiments, either cap piece 510, 510*a* is configured to fit and may be fully employed in conjunction with other disclosed elements of handle 104 as illustrated in FIGS. 5 and 8.

Turning again to FIGS. 14 and 15, disclosed embodiments of first connector 506 may also include a channel 1410 for receiving a bottom portion 1508 of first wing 502 inserted therein. Channel 1410 is configured as a recessed groove and is designed to traverse a circumference of first connector 506. Bottom portion 1508 is dimensioned to fit within the circumferential profile of channel 1410. Select embodiments may provide a snap-fit arrangement to retain bottom portion 1508 once it is fully inserted into channel 1410. In some embodiments, the circumferential length of channel 1410 is dimensioned generally longer that than the circumferential length of bottom portion 1508 inserted therein. Thus, when bottom portion 1508 is inserted within channel 1410 in a final assembly, bottom portion 1508 is capable of traversing within and along channel 1410; the result of which, allows first wing 502 to pivot axially about axis 212 and towards or away from second wing 504. Each of the assembled pieces of the handle assembly, i.e., wings 502, 504, connectors 506, 508, luer connector 1002, may be assembled to one another about a common axis 212 for receiving an insert 202 there through the aforementioned common axis 212.

Turning to FIGS. 5, 8, 11, 12, 13, when pivoting first wing 502 is folded towards second wing 504, one or more first ridges 516 are configured to clear one or more second ridges 518. To do so, embodiments of the present disclosure provide that one or more first ridges 516 are configured horizontally offset from one or more second ridges 518. Accordingly, one or more first ridges 516 do not interfere with one or more second ridges 518 when first wing 502 is folded towards second wing 504. Additionally, first wing 502 and second wing 504 may each be configured to provide a first one or more clearance spaces 542 and a second one or more clearance spaces 544, respectively. In one embodiment clearance space 542 is configured on an interior side 550 of first wing 502 and second one or more clearance spaces 544 is configured on an interior side 552 of second wing 504. In an exemplary embodiment, first one or more clearance spaces 542 are configured horizontally offset from second one or more clearance spaces 544. First one or more clearance spaces 542 may accommodate and receive a corresponding one or more second ridges 518 when first wing 502 is folded completely towards and against second wing 504. In like fashion, second one or more clearance spaces 544 may accommodate and receive the corresponding one or more first ridges 516 when first wing 502 is folded completely towards and against second wing 504. When first wing 502 is folded completely towards and against second wing 504, thereby achieving a fully folded configuration, internal perimeter contact surface 546 of first wing 502 may abut internal perimeter contact surface 548 of second wing 504. In addition, the one or more clearance spaces 542 is dimensioned to receive the one or more second ridges 518, and the one or more clearance spaces 544 is dimensioned to receive the one or more first ridges 516. In the fully folded assembly the configuration of handle 104 generally forms a pistol grip handle formation. Thus, respective wings 502, 504 may be formed as two complimentary pieces of handle 104 that may achieve a completely unfolded configuration, a partially folded configuration, or completely folded configuration thereby forming a pistol grip design.

Tabs 512, 514 form operational and gripping portions for manipulating respective wings 502, 504 by a user. Thus, the offset position of each tab 512, 514 provides elements for manipulation by a user's hand to easily separate folded first wing 502 from second wing 504. These tactile elements form pronounced surfaces to facilitate maneuvering respective wings 502, 504, for example, into or out of fully folded and unfolded positions and/or positions in between. In some disclosed embodiments, tables 512, 514 may be configured to lock together such as to clasp first wing 502 to second wing 504 in a locking engagement.

Figure 13:
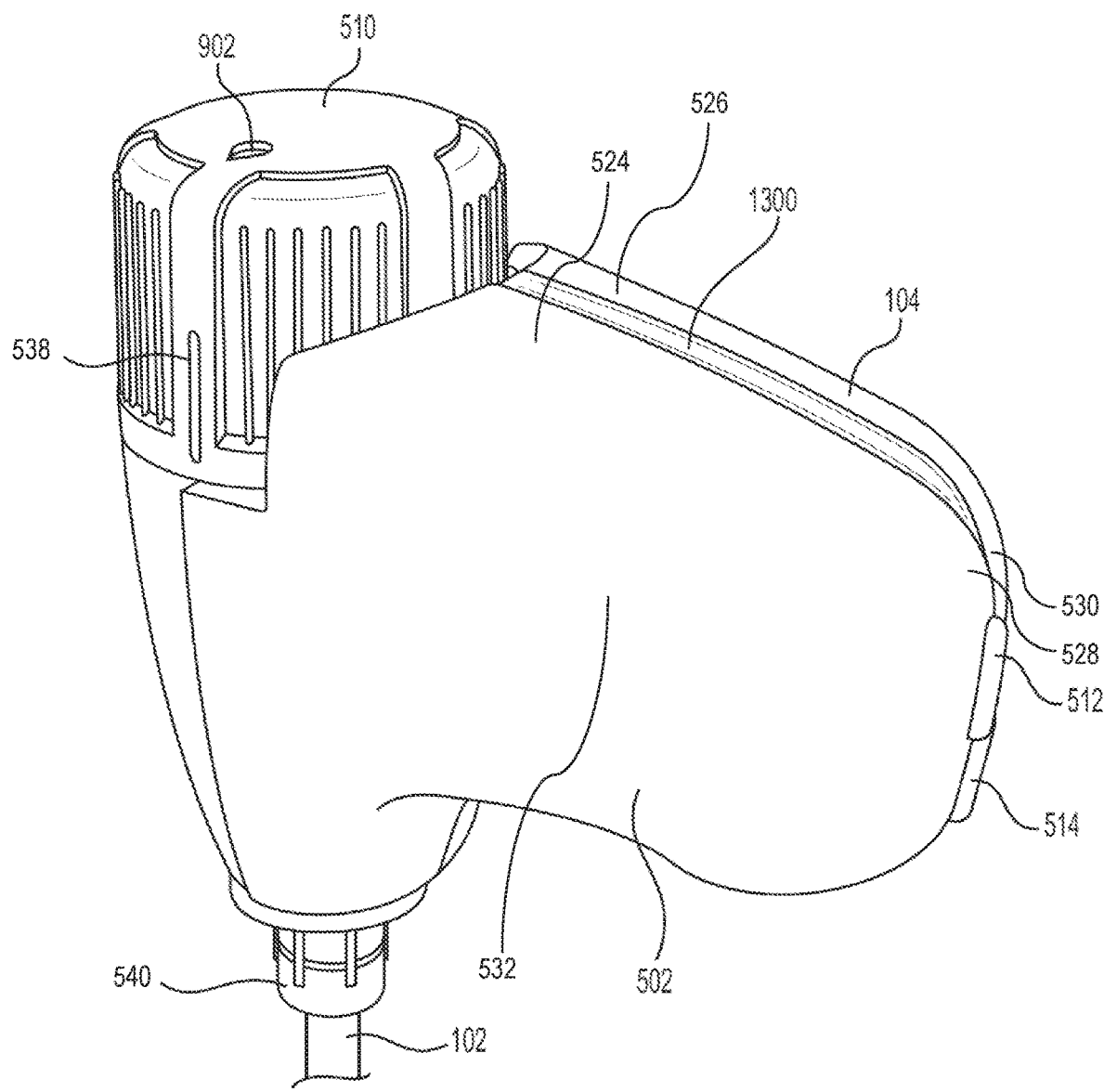
FIG. 13 is an alternate perspective view of the needle apparatus of FIG. 5 with the handle in a completely folded configuration according to one embodiment of the present disclosure.

Likewise, as shown in FIG. 13, a groove or crease 1300 may be formed generally along a meeting ridge or rim of the top surfaces 524, 526 of first and second wings 502, 504, respectively when first wing 502 is completely folded against second wing 504. Groove or crease 1300 may serve as a tactile element facilitating a user to initially and relatively easily separate wings 502, 504, for example, from a folded configuration. The aforementioned elements including tabs 512, 514 and groove or crease 1300 are especially relevant, for example, when a user is wearing gloves, for instance, and attempting to manipulate handle 104.

An injector may also be releasably attachable with handle 104, for example, at threaded center post 1504. The injector can be any part suitable for cement delivery through sheath 102 and into a vertebral body. In the current disclosure, the injector can be a syringe such as the Medallion Syringe from Merit Medical Systems Inc., South Jordan Utah, 84095 U.S.A. Other suitable injectors can be used such as the Dyna Torque Injector from Parallax Medical, Inc., 455 Ravendale Dr., Suite B, Mountain View Calif., 94043, as will occur to those of skill in the art. The syringe can contain cement for injection into inlet 208, through sheath 102 and into a vertebral body.

As will now be apparent to those of skill in the art, needle apparatus 100 can also be used to take a bone or tissue biopsy sample. After needle apparatus 100 is inserted into the patient, insert 202 can be slidably removed from sheath 102. Sheath 102 can then be pushed into the target bone or tissue, effectively coring a biopsy sample there within.

While the embodiments discussed herein are directed to particular implementations of the present disclosure, it will be apparent that the subsets and variations to these embodiments are within the scope of the invention. For example, the first wing 502 and the second wing 504 may be configured in a general T-shape configuration when the handle 104 is in a completely unfolded configuration, and the first wing 502 and the second wing 504 may be configured in a pistol grip configuration in a completely folded configuration. However, the size and shape of the handle can differ. The releasably attachable connector and complementary connector can be any releasable attachment. The end of the needle with the outlet and tip can have two beveled faces thus presenting a substantially continuous leading edge across both the sheath and insert. Each beveled face being substantially continuous and having no step between the sheath and the insert. Alternatively, the end of the needle with the outlet and tip can have more than three beveled faces. Again, each beveled face being substantially continuous and having no step between the sheath and the insert. The end of the needle with the outlet and tip can also be conical, thus presenting a leading point on the insert. Similarly, the sheath and insert are substantially continuously conical and there is no substantial step between the insert and the sheath. The shape of any of the features can differ while still performing the same function. Furthermore, a surface or cone can be considered to be a plurality of edges. Thus, a substantially continuous surface or cone with no step between the insert and sheath can be considered to be a plurality of substantially continuous edges.

Another embodiment for a cement delivery needle apparatus 1700 is illustrated in FIGS. 17-20. In this embodiment, needle apparatus 1700 may comprise some similar configurations, functionality and components as cement delivery needle apparatus 100. For example, needle apparatus 1700 may include a needle 103 and a handle 1704. Needle 103 may be employed with needle apparatus 1700 and include sheath 102 (or cannula) and insert 202 (or stylet). As previously detailed in FIGS. 2A and 2B, insert 202 or stylet is receivably removable within a hollow tubular cavity 214 of sheath 102 for insertion of needle apparatus 1700, for example, into a vertebral body via a percutaneous route. Insert 202 is removable from the sheath 102 to perform subsequent operations such as to facilitate the injection of cement into a vertebral body.

As described in FIGS. 1, 2A, 2B, 3A and 3B, sheath 102 is generally a hollow cylinder with an interior 204, an outlet 206 and an inlet 208. The cross-sectional area of interior 204 is not reduced at outlet 206. The diameter of interior 204 may be substantially constant from inlet 208 to outlet 206. In an exemplary embodiment, sheath 102 is cylindrically centered about axis 212 and has three substantially equal, inwardly beveled surfaces 304 defining outlet 206. Each surface 304 is beveled toward axis 212. Thus, sheath 102 has three sharp points 306 at outlet 206. Each sharp point 306 is present at each intersection of two beveled surfaces 304. Each beveled surface 304 is at substantially the same angle to axis 212. Preferably, each beveled surface 304 is at an angle of from about 15° to about 75°. More preferably, each beveled surface 304 is at an angle of from about 30° to about 60°. In some disclosed embodiments, each beveled surface 304 is at an angle of about 45° to axis 212.

Turning again to FIG. 17, handle 1704 may comprise similar configurations and operate, for example, in a folded (or closed position) and unfolded (or open position) assembly as previously described for handle 104 (for example, with respect to FIGS. 11-13). Thus, handle 1704 may include first wing 502 having first ridges 516 and second wing 504 having second ridges 518. In some disclosed embodiments, first wing 502 may be configured as a rotational component and second wing 504 configured as stationary component of handle 1704 wherein first wing 502 is maneuverable to pivot towards second wing 504 about axis 1712 to configure handle 1704 from an open position to a closed position, respectively.

Handle 1704 may be comprised of multiple pieces including a first connector 1706, a second connector 1708 and a third connector or cap piece 1710. Second connector 1708 and cap piece 1710 may include respective alignment indicator marks 1728 and 1726 to provide an alignment feature of handle 1704. Each component of the first connector 1706 and second connector 1708 and cap piece 1710 may be aligned to fit together axially, for example along axis 1712. In addition, first connector 1706 and second connector 1708 may be telescopically engaged along axis 1712. As evidenced, for example, in FIGS. 17-19, first connector 1706 may be integrally formed with second wing 504 such as being molded together. Likewise, second connector 1708 may be integrally formed with first wing 502 such as being molded together as well. Thus, integrally formed first connector 1706 and second wing 504 is configured in a telescopic assembly with integrally formed second connector 1708 and first wing 502.

Handle 1704 may be appropriately dimensioned to facilitate the ergonomic design of the disclosed invention. In a disclosed configuration, while one or more dimensions may change, handle 1704 is preferably designed ergonomically to be naturally captured or gripped as it is received in the palm of a user's hand for handling and maneuvering.

A visual indicator mark may be disposed, for example, at a top of cap piece 1710. In one embodiment a depressed indicator mark 1702 is formed in the top. Alternatively, a pronounced ridge 902a may be formed along a ridge stemming from the top 904a and transitioning to a side 906a of cap piece 510a (see FIG. 9B). Cap piece 1710 may be generally flat on top and sufficiently sized and strengthened to serve as a striking area. The striking area may be presented to support receiving striking blows to the top of cap piece 1710 by another striking instrument (such as a hammer) that may be employed by a user, for example, during a surgical procedure.

Cap piece 1710, may include ridge lines 908, 908a along its sides 906, and 906a, respectively (see FIGS. 9A and 9B). Ridge lines 908, 908a may be configured as tactile surface projections or indentations for facilitating handling of cap piece 1710 by a user. In all instances, indicator marks 1726, depressed indicator mark 1702, pronounced ridge 902*a*, and ridge lines 908, 908*a*, alone or in combination with indicator mark 1728, serve as visual and/or tactile indicators to a user operating handle 1704, for example, for operational and alignment purpose(s). According to disclosed embodiments, cap piece 1710 is configured to fit and may be fully employed in conjunction with other disclosed elements of handle 1704 as described below.

A cannula hub 1732 is fitted atop of sheath 102 and may interface via retainer mechanism 540. The body 1740 of cannula hub 1732 is configured to be inserted through a hollow interior 1742 of first connector 1706. Hollow interior 1742 may include a keyed cutout 1744 disposed therein. A design of body 1740 may include a prescribed or specialized geometric shape. Keyed cutout 1744 may be configured to correspond as a complimentary geometric shape to body 1740 such as when body 1740 is inserted and received within keyed cutout 1744. In this manner, keyed cutout 1744 is designed and keyed to match the geometrical exterior shape of body 1740 to provide a locked inter-fit connection in a final assembly.

Cannula hub 1732 may be configured to terminate in a threaded connection 1730 at one end. Second connector 1708 may be configured with a hollow interior 1746 such as for receiving spacer insert 1714. Spacer insert 1714 includes an interior bore 1734 which may be configured to correspond to a complimentary geometric shape of body 1740. Thus, interior bore 1734 of spacer insert 1714 may be keyed to match the geometrical exterior shape of body 1740 to provide a locked inter-fit connection in a final assembly. Accordingly, cannula hub 1732, first connector 1706, second connector 1708, spacer insert 1714 and cap piece 1710 may be assembled telescopically such as along center axis 1712. Cap piece 1710 may be configured with complimentary interior grooves to match a threaded connection 1730 of cannula hub 1732. Insert 202 (or stylet) may be connected to cap piece 1710 at one end. In a final assembly, cap piece 1710 is positioned to dispose insert 202 through interior bore 1734, hollow interior 1746 of second connector 1708, hollow interior 1742 of first connector 1706 and through a hollow interior 1748 of cannula hub 1732. Body 1740 and threaded connection 1730 of cannula hub 1732 is inserted through keyed cutout 1744 of hollow interior 1742, hollow interior of second connector 1708, and interior bore 1734 of spacer insert 1714. Threaded connection 1730 of cannula hub 1732 protrudes from interior bore 1734 such that complimentary interior grooves of cap piece 1710 are threaded onto threaded connection 1730 of cannula hub to achieve a final assembly.

Figure 18:
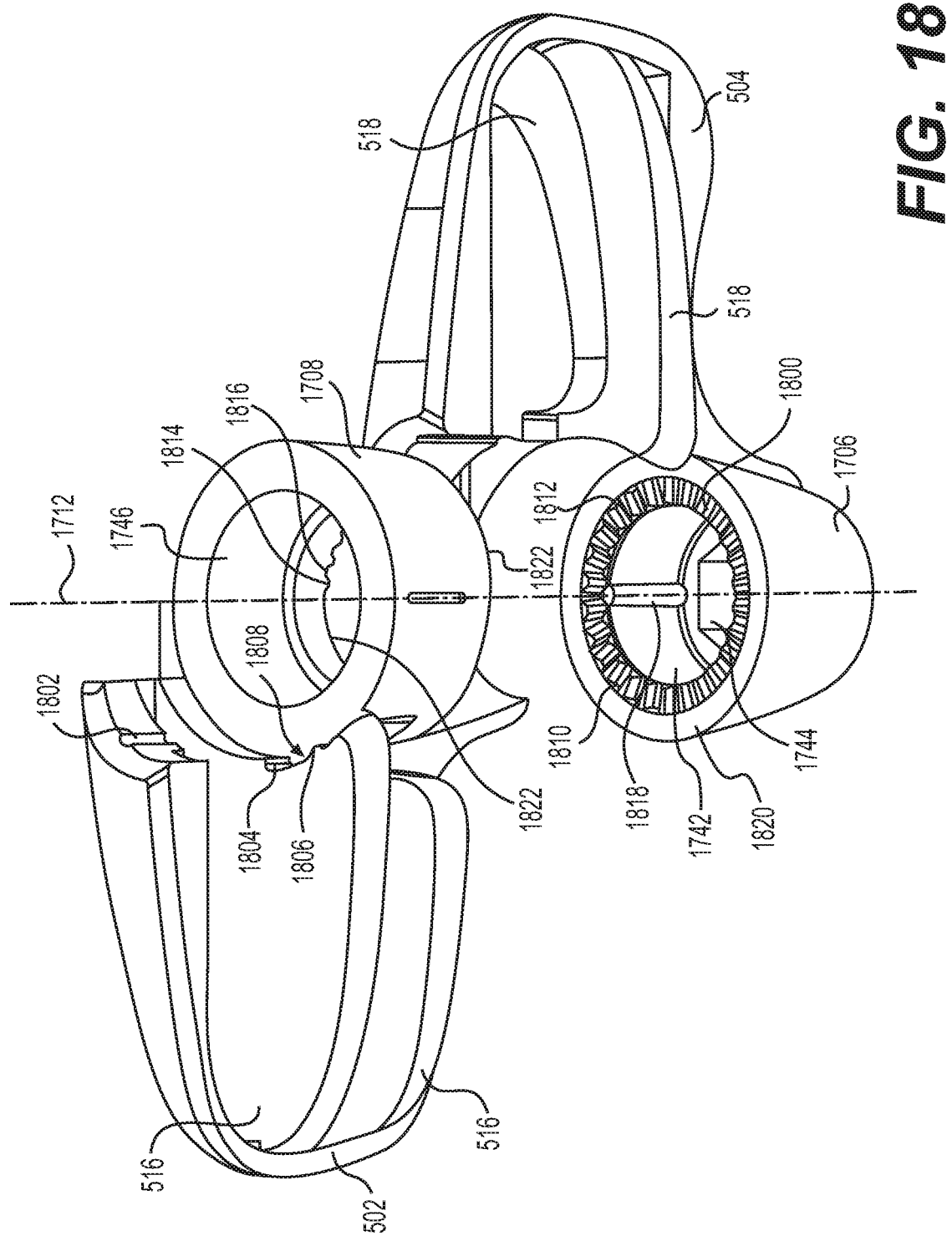
FIG. 18 illustrates an exploded view of the handle configuration of FIG. 17 according to one embodiment of the present disclosure.

A locking feature may be provided for statically retaining cap piece 1710 to handle 1704. In one disclosed embodiment, cap piece 1710 includes tab 1722. As best shown in FIG. 18, an interior surface of first wing 502 includes an indented region 1808 having a hard stop surface 1804 and a locking protrusion 1806. Indented region 1808 is configured as a complimentary shape to the geometrical shape of tab 1722 of cap piece 1710. Thus, when the components of the disclosed invention are assembled, such as along center axis 1712, cap piece 1710 may be rotated to interface tab 1722 past locking protrusion 1806 until it reaches hard stop surface 1804. Thus, at this point, fit tab 1722 is positioned within indented region 1808 and retained therein between hard stop surface 1804 and a locking protrusion 1806 via interference fit.

In another disclosed embodiment, an interior surface region of first wing 502 may be provided with a locking indentation 1802. In some embodiments, locking indentation 1802 may be configured as a groove. Indicator mark 1726 of cap piece 1710 may be configured as a protrusion. A geometrical design of locking indentation 1802 or groove may be complimentary to receive a geometric shape of indicator mark 1726. Thus, when the components of the disclosed invention are assembled, such as along center axis 1712, cap piece 1710 may be rotated with respect to first wing 502 to interface indicator mark 1726 with locking indentation 1802 or groove such that indicator mark 1726 is received within locking indentation 1802 or groove.

Turning again to FIG. 18, another disclosed embodiment illustrates at least a portion of a top surface 1820 of first connector 1706 configured as a toothed wheel 1800. Toothed wheel 1800 may include a plurality of depressions 1810 extending into a surface of first connector 1706 such as along the toothed wheel 1800. In some embodiments, depressions 1810 may include grooves. Toothed wheel 1800 may also include a plurality of protrusions 1812 extending from a surface of first connector 1706 such as along the toothed wheel 1800. Depressions 1810 and protrusions 1812 may be configured in alternating fashion to form the toothed wheel 1800. In some disclosed embodiments, toothed wheel 1800 may be formed directly or integrally into the material of at least a portion of a top surface of first connector 1706, such as via molding processes. In some disclosed applications, the aforementioned material may include ABS material such as that described earlier.

At least a portion of bottom surface 1822 of second connector 1708 may be configured with a complimentary design shape to toothed wheel 1800. It is readily appreciated that the aforementioned complimentary design shape may or may not extend completely around a circumference of bottom surface 1822. In some disclosed embodiments, the complimentary design shape extends around a portion of the circumference of bottom surface 1822, such as around half the diameter of bottom surface 1822. Thus, a region of bottom surface 1822 of second connector 1708 may include protrusions 1814 extending from bottom surface 1822 and depressions 1816 extending into bottom surface 1822. In some embodiments, depressions 1816 may include grooves. It is readily appreciated that in some disclosed embodiments, protrusions 1814 extending from bottom surface 1822 and depressions 1816 extending into bottom surface 1822 may be formed directly or integrally into the material of bottom surface 1822 of second connector 1708, such as via molding processes. In some disclosed applications, the aforementioned material may include ABS material such as that described earlier.

Thus, when the components of the disclosed invention are assembled, such as along center axis 1712, a top surface of first connector 1706 is mated and interfaces with bottom surface 1822 of second connector 1708. In a final assembly, as first wing 502 is pivoted toward second wing 504 about axis 1712, protrusions 1814 of second connector 1708 may be received into depressions 1810 of toothed wheel 1800. In addition protrusions 1812 of toothed wheel 1800 may be received into depressions 1816 of second connector 1708. As rotation of first wing 502 with respect to second wing 504 occurs, protrusions 1814 may be urged into other depressions 1810 and, likewise, protrusions 1812 may also be urged into other depressions 1816. Thus, a toothed wheel assembly may include a toothed wheel 1800 disposed, for example, in at least a portion of top surface 1820 and comprise a plurality of alternating depressions 1810 and protrusions 1812 to match a complimentary plurality of alternating protrusions 1814 and depressions 1816, respectively, along at least a portion of another surface structure such as bottom surface 1822 of second connector 1708. The aforementioned arrangement provides additional control to a user such as when pivoting first wing 502 towards second wing 504, about axis 1712. The interference fit of the toothed wheel assembly may provide a degree of frictional interference and tactile feel, for example, to a user's hand, for enhancing control and maneuverability of components of handle 1704.

Figure 17:
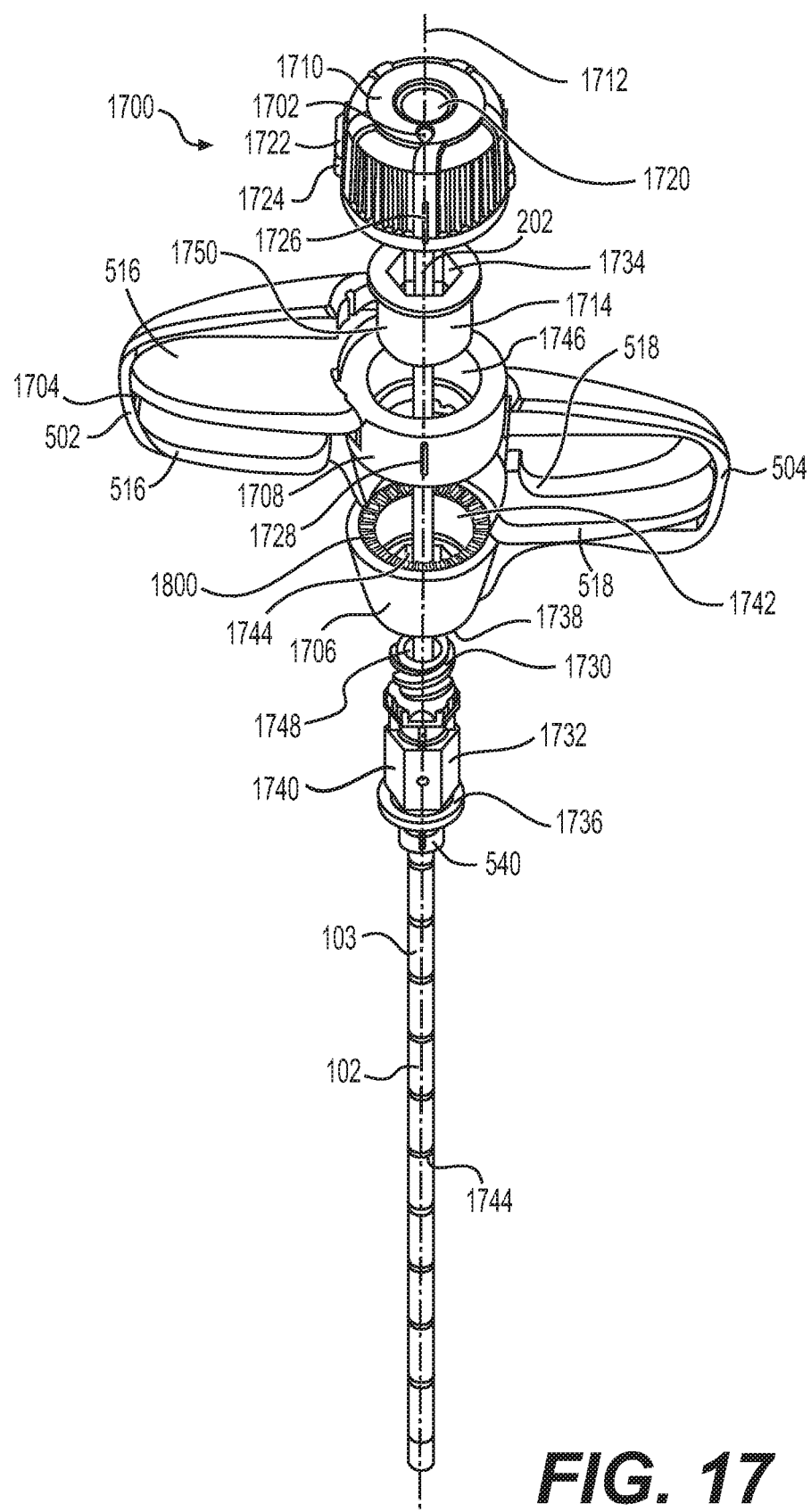
FIG. 17 illustrates a perspective view of another exemplary needle apparatus according to one embodiment of the present disclosure.
Figure 19:
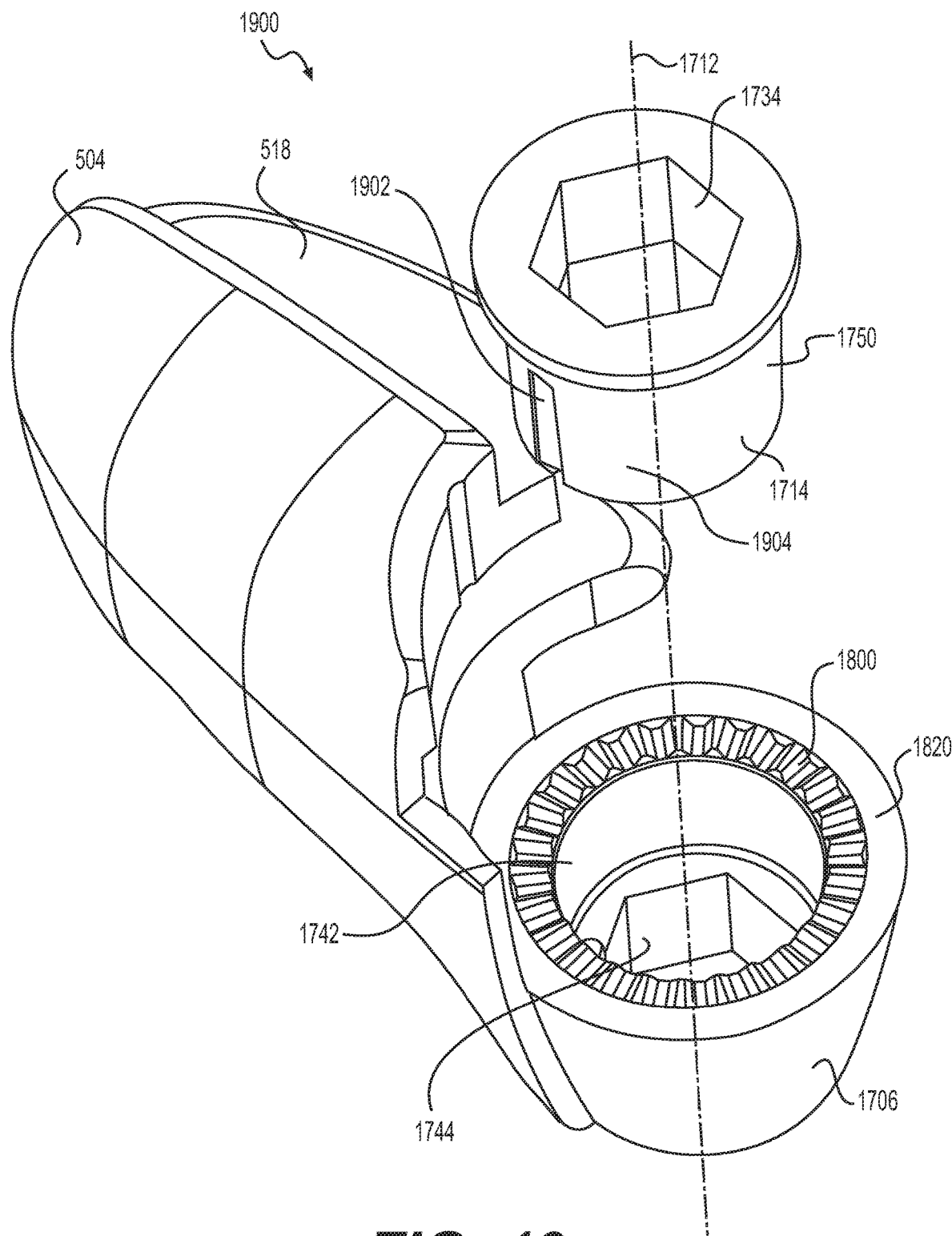
FIG. 19 illustrates another exploded view detailing components of the handle configuration of FIG. 17 according to one embodiment of the present disclosure.

As illustrated in FIG. 18, a protrusion 1818 may be provided along a region of hollow interior 1742 of first connector 1706. In some disclosed embodiments, protrusion 1818 may function as an alignment tab for positioning another component received, for example, hollow interior 1742. Referring to FIGS. 17 and 18, a body portion 1750 of spacer insert 1714 may be geometrically configured to be disposed into and through a hollow interior 1746 of second connector 1708 such as along axis 1712. As illustrated in FIG. 19, spacer insert 1714 may be keyed to include a corresponding slot 1902 formed, for example, into an exterior surface 1904 of body portion 1750. During a final assembly, body portion 1750 may further extend through hollow interior 1746 of second connector 1708 and into hollow interior 1742 of first connector 1706 such as along axis 1712. Additionally, spacer insert 1714 may be manipulated to align corresponding slot 1902 with protrusion 1818 as body portion 1750 is positioned and received within hollow interior 1742. Disposed in the aforementioned position, spacer insert 1714 is aligned within hollow interior 1742 of first connector 1706 in accordance with one preferred disclosed embodiment.

The present disclosure provides a novel cement delivery needle for expressing bone cement or a suitable biomaterial into a vertebral body. In one embodiment there is provided a cement delivery needle with a sheath and an insert receivably removable within the sheath. The sheath has an interior, an outlet, and an inlet. The insert has a tip and an opposing end. The tip of the insert and the outlet of the sheath are tapered and alignable such that they present a continuous edge when the insert is received within the sheath. Because there is no step between the sheath and the insert the cement delivery needle can be easier to insert into the patient. Insertion of the needle can require less applied force and the use of a hammer can be avoided when the needle passes through the periosteum into the pedicle and in the transition from the pedicle into the vertebral body. Further, less required force can allow the operator greater control during insertion of the needle. Also, the cement can be delivered to the vertebral body more easily as the cross sectional area of the interior of the sheath is not reduced at the outlet of the sheath. The cement also disperses easily from the beveled edges, thus more cement can be delivered to the vertebral body.

Having described the many embodiments of the present disclosure in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated. For example other embodiments and configurations of handles may replace the disclosed handle 104 of the present disclosure. In some instances, alternate embodiments of the disclosed handle are provided to present alternative ergonomic designs, feeling and gripping action to the handle for varying preferences to respective users. Examples of alternate handle designs are illustrated, for example, in FIGS. 16A-16L.

All publications, patents and patent applications referred to herein are incorporated by reference in their entirety to the same extent as if each individual publication, patent or patent application was specifically and individually indicated to be incorporated by reference in its entirety.

While the present disclosure has been disclosed with references to certain embodiments, numerous modification, alterations, and changes to the described embodiments are possible without departing from the sphere and scope of the present disclosure, as defined in the appended claims. Accordingly, it is intended that the present disclosure not be limited to the described embodiments, but that it has the full scope defined by the language of the following claims, and equivalents thereof.

What is claimed is:

1. A handle apparatus wherein the handle apparatus comprises:
   a first wing; and
   a second wing;
   wherein the first wing and the second wing are configured to pivot about a common axis to one another;
   wherein the first wing has one or more first ridges, and a first one or more clearance spaces;
   wherein the second wing has one or more second ridges, and a second one or more clearance spaces, and
   wherein the one or more first ridges is configured to be received within the second one or more clearance spaces and the one or more second ridges is configured to be received within the first one or more clearance spaces when the first wing is pivoted about the common axis to the second wing in a folded configuration; and
   a first connector;
   a second connector;
   a third connector; and,
   wherein the second connector is telescopically engaged with the first connector along the common axis.

2. The handle apparatus of claim 1, wherein the third connector has a cap piece that is configured to be releasably attached to the handle.

3. The handle apparatus of claim 2, wherein the handle apparatus is configured with a locking mechanism to lock the cap piece to the handle.

4. The handle apparatus of claim 3, wherein the locking mechanism comprises a luer lock.

5. The handle apparatus of claim 2, wherein the locking mechanism comprises:
   a tab disposed on the cap piece; and
   an indented region formed on a portion of the handle,
   wherein the cap piece is configured to rotate along the common axis to dispose the tab within the indented region formed in the portion of the handle.

6. The handle apparatus of claim 2, wherein the cap piece is sufficiently designed to withstand a striking force as a point of contact to the handle.

7. The handle apparatus of claim 2, wherein the cap piece comprises a top generally raised above respective exterior top surfaces of the first wing and the second wing.

8. The handle apparatus of claim 1, wherein the first connector is integrally formed with the second wing and the second connector is integrally formed the first wing.

9. The handle apparatus of claim 1, wherein a portion of the first wing is configured to be received within a portion of the second connector in a mated relationship along the common axis.

10. The handle apparatus of claim 1, wherein the third connector and the second connector comprise an alignment feature.

11. The handle apparatus of claim 10, wherein the alignment feature comprises alignment indicia on the third connector and the second connector.

12. The handle apparatus of claim 11, wherein an audible sound occurs when the alignment of the third connector and the second connector is obtained.

13. The handle apparatus of claim 12, wherein the audible sound is an audible snap.

14. The handle apparatus of claim 1,
wherein a surface of the first connector includes a plurality of depressions and protrusions,
wherein a surface of the second connector includes a plurality of depressions and protrusions,
wherein in a final assembly, the surface of the first connector is in mated arrangement with the surface of the second connector,
wherein the protrusions of the second connector fit into complimentary depressions of the first connector, and depressions of the second connector are received by complimentary protrusions of the first connector.

15. A needle apparatus comprising:
a foldable handle;
a sheath connected to the foldable handle;
an insert disposed through the foldable handle and through the sheath; and
a locking mechanism for retaining the insert to the foldable handle;
wherein the foldable handle comprises:
a first wing; and
a second wing;
wherein the first wing and the second wing are configured to pivot about a common axis to one another;
wherein the first wing has one or more first ridges, and a first one or more clearance spaces;
wherein the second wing has one or more second ridges, and a second one or more clearance spaces,
wherein the one or more first ridges is configured to be received within the second one or more clearance spaces and the one or more second ridges is configured to be received within the first one or more clearance spaces when the first wing is pivoted about the common axis to the second wing in a folded configuration; and
a first connector;
a second connector; and
a third connector,
wherein the second connector is telescopically engaged with the first connector along the common axis.

16. The needle apparatus of claim 15, wherein the first connector is integrally formed with the second wing and the second connector is integrally formed the first wing.

17. The needle apparatus of claim 16, wherein a portion of the first wing is configured to be received within a portion of the second connector in a mated relationship along the common axis.

18. The needle apparatus of claim 15,
wherein a surface of the first connector includes a plurality of depressions and protrusions,
wherein a surface of the second connector includes a plurality of depressions and protrusions,
wherein in a final assembly, the surface of the first connector is in mated arrangement with the surface of the second connector,
wherein the protrusions of the second connector fit into complimentary depressions of the first connector, and depressions of the second connector are received by complimentary protrusions of the first connector.

19. The needle apparatus of claim 15, wherein a needle comprises the insert disposed through the sheath.

20. The needle apparatus of claim 19, wherein the insert is a stylet and the sheath is a cannula.

* * * * *